US005747253A

United States Patent [19]

Ecker et al.

[11] Patent Number: 5,747,253
[45] Date of Patent: *May 5, 1998

[54] COMBINATORIAL OLIGOMER IMMUNOABSORBANT SCREENING ASSAY FOR TRANSCRIPTION FACTORS AND OTHER BIOMOLECULE BINDING

[75] Inventors: David J. Ecker, Leucadia; Tim Vickers, Oceanside; Pete Davis, Carlsbad, all of Calif.

[73] Assignee: Isis Pharmaceuticals, Inc., Carlsbad, Calif.

[ * ] Notice: The term of this patent shall not extend beyond the expiration date of Pat. No. 5,698,391.

[21] Appl. No.: 386,141

[22] Filed: Feb. 8, 1995

Related U.S. Application Data

[63] Continuation-in-part of Ser. No. 357,396, Dec. 16, 1994, which is a continuation-in-part of Ser. No. 196,103, filed as PCT/US92/07121, Aug. 21, 1992, which is a continuation-in-part of Ser. No. 749,000, Aug. 23, 1991, abandoned.

[51] Int. Cl.$^6$ .................... C12Q 1/68; G01N 33/53; C07H 21/00
[52] U.S. Cl. .................... 435/6; 435/7.1; 536/24.1; 536/25.3
[58] Field of Search .................... 435/5, 6, 7.1; 536/24.1, 536/25.3

[56] References Cited

U.S. PATENT DOCUMENTS

| 4,833,092 | 5/1989 | Geysen | 436/501 |
|---|---|---|---|
| 5,010,175 | 4/1991 | Rutter et al. | 530/334 |
| 5,034,506 | 7/1991 | Summerton et al. | 528/391 |
| 5,194,392 | 3/1993 | Geysen | 436/518 |

FOREIGN PATENT DOCUMENTS

| 0 302 758 A1 | 2/1989 | European Pat. Off. . |
| WO 84/03564 | 9/1984 | WIPO . |
| 86/00991 | 2/1986 | WIPO . |
| WO 87/01374 | 3/1987 | WIPO . |
| WO 91/10671 | 7/1991 | WIPO . |
| WO 91/11535 | 8/1991 | WIPO . |
| WO 91/12331 | 8/1991 | WIPO . |
| WO 92/02258 | 2/1992 | WIPO . |
| WO 92/03452 | 3/1992 | WIPO . |
| WO 92/05285 | 4/1992 | WIPO . |
| WO 92/09300 | 6/1992 | WIPO . |
| WO 92/18522 | 10/1992 | WIPO . |

OTHER PUBLICATIONS

Matthews et al. Analytical Biochemistry 169 1–25 (1988) Analytical Strategies for the Use of DNA Probes.
Blackwell et al. Science 250 1149–1151 (1990) Sequence Specific DNA Binding by the c-Myc Protein.
Gilmore Cancer Surveys 15 69–87 (1992) Role of rel Family Genes in Normal and Malignant Lymphoid Cell Growth.
Bielinska et al., "Regulation of Gene Expression with Double-Stranded Phosphorothioate Oligonucleotides" Science 250: 997–1000 (1990).
Blackwell et al., "Sequence-Specific DNA Binding by the c-Myc Protein", Science 250: 1149–1151 (1990).
Blackwell and Weintraub, "Differences and Similarities in DNA-Binding Preferences of MyoD and E2A Protein Complexes Revealed by Binding Site Selection", Science 250: 1104–1110 (1990).
Bock. et al., "Selection of Single-Stranded DNA Molecules that Bind and Inhibit Human Thrombin", Nature 355: 564–566 (1992).
Chittenden et al., "The T/E1A-Binding Domain of the Retinoblastoma Product Can Interact Selectively with a Sequence-Specific DNA-Binding Protein", Cell 65: 1073–1082 (1991).
Cook, P.D., "Medicinal Chemistry of Antisense Oligonucleotides—Future Opportunities", Anti-Cancer Drug Design 6: 585–607 (1991).
Cullen et al., "The HIV-1 Tat Protein: An RNA Sequence-Specific Processivity Factor", Cell 63: 655–657 (1990).
Dustin and Springer. "Lymphocyte Function-Associated Antigen-1 (LFA-1) Interaction with Intercellular Adhesion Molecule-1 (ICAM-1) is One of At Least Three Mechanisms for Lymphocyte Adhesion to Cultured Endothelial Cells", J. Cell. Biol. 107: 321–331 (1988).
Ellington and Szostak, "In Vitro Selection of RNA Molecules that Bind Specific Ligands", Nature 346: 818–822 (1990).
Fodor et al., "Light-Directed, Spatially Addressable Parallel Chemical Synthesis", Science 251: 767–773 (1991).
Franza et al., "Characterization of Cellular Proteins Recognizing the HIV Enhancer Using a Microscale DNA-Affinity Precipitation Assay", Nature 330: 391–395 (1987).
Geysen et al., "Strategies for Epitope Analysis Using Peptide Synthesis", J. Immunol. Meth. 102: 259–274 (1987).
Gilmore and Temin, "Different Localization of the Product of the v-rel Oncogene in Chicken Fibroblasts and Spleen Cells Correlates with Transformation by REV-T", Cell 44: 791–800 (1986).
Goodchild, "Conjugates of Oligonucleotides and Modified Oligonucleotides: A Review of Their Synthesis and Properties", Bioconjugate Chemistry 1: 165–187 (1990).
Green et al., "In Vitro Genetic Analysis of the Tetrahymena Self-Splicing Intron", Nature 347: 406–408 (1990).

(List continued on next page.)

Primary Examiner—James Ketter
Assistant Examiner—John S. Brusca
Attorney, Agent, or Firm—Woodcock Washburn Kurtz Mackiewicz & Norris LLP

[57] ABSTRACT

Methods useful for the determination of oligomers which have specific activity for a transcription factor or other target molecule from a pool of primarily randomly assembled subunits are provided. The disclosed methods involve repeated syntheses of increasingly simplified sets of oligomers coupled with novel selection procedures for determining oligomers having the highest activity. Freedom from the use of enzymes allows the application of these methods to any molecules which can be oligomerized in a controlled fashion.

68 Claims, 9 Drawing Sheets

OTHER PUBLICATIONS

Hegde et al., "Crystal Structure at 1.7 A of the Bovine Papillomavirus-1 E2 DNA-Binding Domain Bound to its DNA Target", *Nature* 359: 505–512 (1992).

Houghton et al., "Generation and Use of Synthetic Peptide Combinatorial Libraries for Basic Research and Drug Discovery", *Nature* 354: 84–86 (1991).

Joyce, "Amplification, Mutation and Selection of Catalytic RNA", *Gene* 82: 83–87 (1989).

Kinzler and Vogelstein, "The GLI Gene Encodes a Nuclear Protein Which Binds Specific Sequences in the Human Genome", *Molec. Cell. Biol.* 10: 634–642 (1990).

Kinzler and Vogelstein, "Whole Genome PCR: Application to the Identification of Sequences Bound by Gene Regulatory Proteins", *Nucleic Acid Research* 17: 3645–3653 (1989).

König et al., "Autoregulation of fos: the Dyad Symmetry Element as the Major Target of Repression", *EMBO Journal* 8: 2559–2566 (1989).

Kristie and Roisman, "α4, The Major Regulatory Protein of Herpes Simplex Virus Type 1, is Stably and Specifically Associated with Promoter–Regulatory Domains of α Genes and of Selected Other Viral Genes", *Proc. Natl. Acad. Sci.* 83: 3218–3222 (1986).

Lam et al., "A New Type of Synthetic Peptide Library for Identifying Ligand–Binding Acivity", *Nature* 354: 82–84 (1991).

Mason et al., "Diversity of the Antibody Response", *Vaccines* 86: 97–103 (1986).

Nielsen et al., "Sequence–Selective Recognition of DNA by Strand Displacement with a Thymine–Substituted Polyamide", *Science* 254: 1497–1500 (1991).

Niller and Hennighausen, "Formation of Several Specific Nucleoprotein Complexes on the Human Cytomegalovirus Immediate Early Enhancer", *Nucleic Acids Research* 19: 3715–3721 (1991).

Nisen et al., "Enhanced Expression of the N-myc Gene in Wilms' Tumors", *Cancer Research* 46: 6217–6222 (1986).

Oliphant et al., "Defining the Sequence Specificity of DNA-Binding Proteins by Selecting Binding Sites from Random-Sequence Oligonucleotides: Analysis of Yeast GCN4 Protein", *Mol. Cell. Biol.* 9: 2944–2949 (1989).

Oliphant and Struhl, "Defining the Consensus Sequences of *E. coli* Promoter Elements by Random Selection", *Nucleic Acids Research* 16: 7673–7683 (1988).

Owens et al., "The Rapid Identification of HIV Protease Inhibitors Through the Synthesis and Screening of Defined Peptide Mixtures", *Biochem. Biophys. Res. Commun.* 181: 402–408 (1991).

Robertson and Joyce, "Selection In Vitro of an RNA Enzyme That Specifically Cleaves Single–Stranded DNA", *Nature* 344: 467–468 (1990).

Sharp and Marciniak, "HIV Tar: An RNA Enhancer?", *Cell* 59: 229–230 (1989).

Thiesen and Bach, "Target Detection Assay (TDA): A Versatile Procedure to Determine DNA Binding Sites as Demonstrated on SP1 Protein", *Nucleic Acid Research* 18: 3203–3209 (1990).

Tuerk and Gold, "Systematic Evolution of Ligands by Exponential Enrichment: RNA Ligands to Bacteriophage T4 DNA Polymerase", *Science* 249: 505–510 (1990).

Uhlmann and Peyman, "Antisense Oligonucleotides: A New Therapeutic Principle", *Chemical Reviews*, 1990, 90: 543–584 (1990).

Van der Zee et al., "Efficient Mapping and Characterization of a T Cell Epitope by the Simultaneous Synthesis of Multiple Peptides", *Eur. J. Immunol.* 19: 43–47 (1989).

Vickers, et al., "Inhibition of HIV–LTR Gene Expression by Oligonucleotides Targeted to the TAR Element", *Nucleic Acid Research* 19: 3359–3368 (1991).

Yamada, "Adhesive Recognition Sequences", *J. Biol. Chem.* 266: 12809–12812 (1991).

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
( A ) LENGTH: 47 base pairs
( B ) TYPE: nucleic acid
( C ) STRANDEDNESS: single
( D ) TOPOLOGY: linear ( i i ) MOLECULE TYPE: RNA (genomic)

( x i ) SEQUENCE DESCRIPTION: SEQ ID NO:1:

GGUGGUGGUG GGCGCCGUCG GUGUGGGCAA GAGUGCGCUG ACCAUCC     47

( 2 ) INFORMATION FOR SEQ ID NO:2:

( i ) SEQUENCE CHARACTERISTICS:
  ( A ) LENGTH: 10 base pairs
  ( B ) TYPE: nucleic acid
  ( C ) STRANDEDNESS: single
  ( D ) TOPOLOGY: linear ( i i ) MOLECULE TYPE: RNA (genomic)

( i x ) FEATURE:
  ( A ) NAME/KEY: misc_feature
  ( B ) LOCATION: 4
  ( D ) OTHER INFORMATION: /note= "pyrene analog of adenine"

( x i ) SEQUENCE DESCRIPTION: SEQ ID NO:2:

NNNANGNNNN  10

( 2 ) INFORMATION FOR SEQ ID NO:3:

( i ) SEQUENCE CHARACTERISTICS:
  ( A ) LENGTH: 10 base pairs
  ( B ) TYPE: nucleic acid
  ( C ) STRANDEDNESS: single
  ( D ) TOPOLOGY: linear ( i i ) MOLECULE TYPE: RNA (genomic)

( i x ) FEATURE:
  ( A ) NAME/KEY: misc_feature
  ( B ) LOCATION: 4
  ( D ) OTHER INFORMATION: /note= "pyrene analog of adenine"

( x i ) SEQUENCE DESCRIPTION: SEQ ID NO:3:

NNNANANNNN  10

( 2 ) INFORMATION FOR SEQ ID NO:4:

( i ) SEQUENCE CHARACTERISTICS:
  ( A ) LENGTH: 10 base pairs
  ( B ) TYPE: nucleic acid
  ( C ) STRANDEDNESS: single
  ( D ) TOPOLOGY: linear ( i i ) MOLECULE TYPE: RNA (genomic)

( i x ) FEATURE:
  ( A ) NAME/KEY: misc_feature
  ( B ) LOCATION: 4
  ( D ) OTHER INFORMATION: /note= "pyrene analog of adenine"

( x i ) SEQUENCE DESCRIPTION: SEQ ID NO:4:

NNNANCNNNN  10

( 2 ) INFORMATION FOR SEQ ID NO:5:

( i ) SEQUENCE CHARACTERISTICS:
  ( A ) LENGTH: 10 base pairs
  ( B ) TYPE: nucleic acid
  ( C ) STRANDEDNESS: single
  ( D ) TOPOLOGY: linear ( i i ) MOLECULE TYPE: RNA (genomic)

( i x ) FEATURE:
  ( A ) NAME/KEY: misc_feature
  ( B ) LOCATION: 4
  ( D ) OTHER INFORMATION: /note= "pyrene analog of adenine"

( x i ) SEQUENCE DESCRIPTION: SEQ ID NO:5:

NNNANUNNNN  10

( 2 ) INFORMATION FOR SEQ ID NO:6:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:6:

CCCUUCCANU C            11

( 2 ) INFORMATION FOR SEQ ID NO:7:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:7:

CCCUUCCGNU C            11

( 2 ) INFORMATION FOR SEQ ID NO:8:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:8:

CCCUUCCCNU C            11

( 2 ) INFORMATION FOR SEQ ID NO:9:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:9:

CCCUUCCUNU C            11

( 2 ) INFORMATION FOR SEQ ID NO:10:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:10:

CCCUUCCCAU C            11

( 2 ) INFORMATION FOR SEQ ID NO:11:

( i ) SEQUENCE CHARACTERISTICS:

( A ) LENGTH: 11 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:11:

CCCUUCCCGU C         11

( 2 ) INFORMATION FOR SEQ ID NO:12:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:12:

CCCUUCCCCU C         11

( 2 ) INFORMATION FOR SEQ ID NO:13:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:13:

CCCUUCCCUU C         11

( 2 ) INFORMATION FOR SEQ ID NO:14:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:14:

GCGNNNANNN NNCGC         15

( 2 ) INFORMATION FOR SEQ ID NO:15:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:15:

GCGNNNGNNN NNCGC         15

( 2 ) INFORMATION FOR SEQ ID NO:16:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:16:

GCGNNNCNNN NNCGC    15

( 2 ) INFORMATION FOR SEQ ID NO:17:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:17:

GCGNNNUNNN NNCGC    15

( 2 ) INFORMATION FOR SEQ ID NO:18:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

AAGACGTCTT GCG    13

( 2 ) INFORMATION FOR SEQ ID NO:19:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

TCTGCAGAAC GC    12

( 2 ) INFORMATION FOR SEQ ID NO:20:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:20:

GCCAGAUCUG AGCCUGGGAG CUCUCUGGC    29

( 2 ) INFORMATION FOR SEQ ID NO:21:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:21:

CUGGCCUUCC UACAAGGGAA GGCCAG    26

( 2 ) INFORMATION FOR SEQ ID NO:22:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 26
        ( D ) OTHER INFORMATION: /note= "biotin labeled"

( x i ) SEQUENCE DESCRIPTION: SEQ ID NO:22:

GGGGACTTTC CGCTGGGACT TTCTAG        26

( 2 ) INFORMATION FOR SEQ ID NO:23:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 26
        ( D ) OTHER INFORMATION: /note= "biotin labeled"

( x i ) SEQUENCE DESCRIPTION: SEQ ID NO:23:

CTGGAAAGTC CCAGCGGAAG GTCCCC        26

( 2 ) INFORMATION FOR SEQ ID NO:24:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:24:

CCANNANNNN GCCUGGGAGC NNNNUGG        27

( 2 ) INFORMATION FOR SEQ ID NO:25:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:25:

CCANNGNNNN GCCUGGGAGC NNNNUGG        27

( 2 ) INFORMATION FOR SEQ ID NO:26:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:26:

CCANNCNNNN GCCUGGGAGC NNNNUGG         27

( 2 ) INFORMATION FOR SEQ ID NO:27:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:27:

CCANNUNNNN GCCUGGGAGC NNNNUGG         27

( 2 ) INFORMATION FOR SEQ ID NO:28:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 25
        ( D ) OTHER INFORMATION: /note= "biotin labeled"

( x i ) SEQUENCE DESCRIPTION: SEQ ID NO:28:

GATCCCCCCA CCACGTGGTG CCTGA         25

( 2 ) INFORMATION FOR SEQ ID NO:29:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 25
        ( D ) OTHER INFORMATION: /note= "biotin labeled"

( x i ) SEQUENCE DESCRIPTION: SEQ ID NO:29:

GATCTCAGGC ACCACGTGGT GGGGG         25

( 2 ) INFORMATION FOR SEQ ID NO:30:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:30:

GCGNNNANNN NNNCGC         16

( 2 ) INFORMATION FOR SEQ ID NO:31:

( i ) SEQUENCE CHARACTERISTICS:

```
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:31:

GCGNNNGNNN NNNCGC                                                   16

( 2 ) INFORMATION FOR SEQ ID NO:32:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:32:

GCGNNNCNNN NNNCGC                                                   16

( 2 ) INFORMATION FOR SEQ ID NO:33:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:33:

GCGNNNUNNN NNNCGC                                                   16
```

COMBINATORIAL OLIGOMER IMMUNOABSORBANT SCREENING ASSAY FOR TRANSCRIPTION FACTORS AND OTHER BIOMOLECULE BINDING

CROSS REFERENCE TO RELATED APPLICATIONS

The present application is a continuation-in-part of U.S. Ser. No. 08/357,396 filed Dec. 16, 1994, which is a continuation-in-part of U.S. Ser. No. 08/196,103 filed Feb. 22, 1994, which is the U.S. national phase of international application Serial No. PCT/US92/07121 filed Aug. 21, 1992, which is a continuation-in-part of U.S. Ser. No. 07/749,000 filed Aug. 23, 1991, now abandoned, all applications being incorporated herein by reference.

FIELD OF THE INVENTION

This invention relates to the identification of oligomers useful for therapeutic, diagnostic, and research applications. In particular it relates to oligomers which bind to specific transcription factors and modulate their function in cells.

BACKGROUND OF THE INVENTION

Transcription factors are DNA or, in a few cases, RNA binding proteins which regulate the expression of genes. These key proteins thereby control the production of all the other proteins in the cell. Viruses which infect cells and cause disease encode their own transcription factors which specifically regulate expression of the viral genes. Examples of virally encoded transcription factors which regulate viral gene expression are the human papillomavirus #2 protein, Hegde, et al., *Nature* 1992, 354, 505, the herpes simplex virus α4 protein, Kristie, et al., *Proc.Natl.Acad.Sci.* 1986, 83, 3218, the human cytomegalovirus immediate early proteins, Niller, et al., *Nucleic Acids Research* 1991, 19, 3715, and the human immunodeficiency virus tat protein, Sharp, et al., *Cell* 1989, 59, 229. Specific binding to any of these proteins might interfere with the normal life cycle of the virus and provide therapeutic benefits. Transcription factors of normal cellular origin might also be targeted to achieve therapeutic objectives. In certain disease states such as cancer or inflammation, transcription factors such as the fos/jun proteins, Konig, et al., *EMBO Journal* 1989, 8, 2559, or the C-MYC protein, Blackwell, et al., *Science* 1990, 250, 1149 are links in a chain of signal transduction gone awry. Interference with specific transcription factors might be used as a means to restore a more normal cellular phenotype.

Oligomers may be designed which are useful for therapeutic, diagnostic and research applications, such as binding to specific transcription factors. In the past, development of biologically active oligomer substances was often limited to the modification of known sequences, unit by unit, until a desired characteristic or efficacy was achieved. For example, Androphy, et al., U.S. Ser. No. 302,758 issued 1989, have described methods to bind to the papilloma E2 transcription factor using DNA decoys which have homology to the natural E2 recognition sequence, Bielinska, et al., *Science* 1990, 250, 997, have also described regulation of gene expression with double stranded phosphorothioate oligonucleotides targeted to HIV. Holcenberg, et al., U.S. Pat. No. 9,111,535 issued 1991, describe double stranded phosphorothioate oligomers which bind to viral or cellular transcriptional proteins. Chu, et al., U.S. Pat. No. 9,218,522 issued 1992, describe oligonucleotides useful on decoys for DNA binding proteins which are equipped with reagents that cross link the proteins to the decoys. While in each of these cases some degree of success is reported, the number of molecules tested for binding is small. In addition to time drawbacks, protocols employing these types of methodologies are limiting in that the final product is based upon, and often not far removed from, the structure of the starting material. Availability of sufficient quantities of transcription factor further limits the usefulness of these and other methodologies.

Recently, new methods have been developed whereby drugs and biologically active substances can be discovered through "combinatorial strategies," which is the chemical or enzymatic synthesis of a very large number of different molecules coupled with a screening technique to identify one molecule from the library with desired properties. A variety of combinatorial strategies have been described to identify active peptides as Houghton, et al. *Nature* 1991, 354, 84; Lam, et al., *Nature* 1991, 354, 82; Owens, et al., *Biochem. Biophys. Res. Commun.* 1991, 181, 402; Foder, et al., *Science* 1991, 251, 767; Geysen, et al.. *Molecular Immunology* 1992, 89, 4505; Rutter, et al., U.S. Pat. No. 5,010,175 issued Apr. 23, 1992.

Focusing on the field of nucleic acid—protein binding, combinatorial nucleic acid selection methods generally select for a specific nucleic acid sequence from a pool of random nucleic acid sequences based on the ability of selected sequences to bind to a target protein. The selected sequences are then amplified and the selection process repeated until a few strongly binding sequences are identified. These methods generally employ enzymatic steps within the protocol. T7 RNA polymerase and Taq I associated with polymerase chain reaction amplification methods are commonly employed. One group recently identified a target sequence to the RNA-binding protein gp43. Tuerk and Gold, *Science* 1990 249, 505. Tuerk and Gold's "systematic evolution of ligands by exponential enrichment" (SELEX) method identified specifically bindable RNA sequences using four cycles of amplification of RNA sequences having variable portions therein and which were specifically bindable to gp43.

Another group designed DNA molecules which recognized the protease thrombin. Bock, et al., *Nature* 1992, 355, 564. This method involves the preparation of a population involving a random region flanked by known primer regions followed by PCR amplification and selection. Small molecule mimics of metabolic cofactors have been selectively recognized by RNA sequences in this manner by Ellington and Szostak, *Nature* 1990, 346, 818.

Weintraub has described methods for the identification of protein specific oligonucleotide sequences. Weintraub, et al., WO 92/05285, issued Apr. 2, 1993, teaches binding of a complex mixture of oligonucleotide containing random sequences and using PCR to identify the best sequence. Oliphant et al., *Nucleic Acids Research*, 1988, 16, 7673 and Oliphant, et al., *Mol.Cell. Biol.*, 1989, 9, 2944 used in vivo selection methods to define the sequence recognition properties of DNA binding proteins.

These techniques were suggested to be useful to design oligonucleotide ligands, however their dependence upon enzymatic means for amplification and sequence determination limits their uses. Simpler methods for the identification of useful oligomers which are specifically bindable to transcription factors and other target molecules and which express specific activity for transcription factors and other target molecules are greatly desired. Methods which are not dependent upon enzymatic means would simplify protocols as well as expand the range of substrates with which the protocols would be effective. For example, presently there are over one hundred nucleotide analogs available. Cook, P. D., *Anti-Cancer Drug Design* 1991, 6, 585 and Uhlmann, et al., *Chem. Rev.* 1990, 90, 544. Since not all analogs are amenable to enzymatic processes, a non-enzymatic means for determining useful oligomer sequences which are specifically bindable to transcription factors and other target molecules is greatly desired. Such methods could determine oligomers which are specifically bindable, not only to natural DNA- or RNA-binding proteins, but also to any protein, nucleic acid, or other target molecule.

SUMMARY OF THE INVENTION

Figure 1:
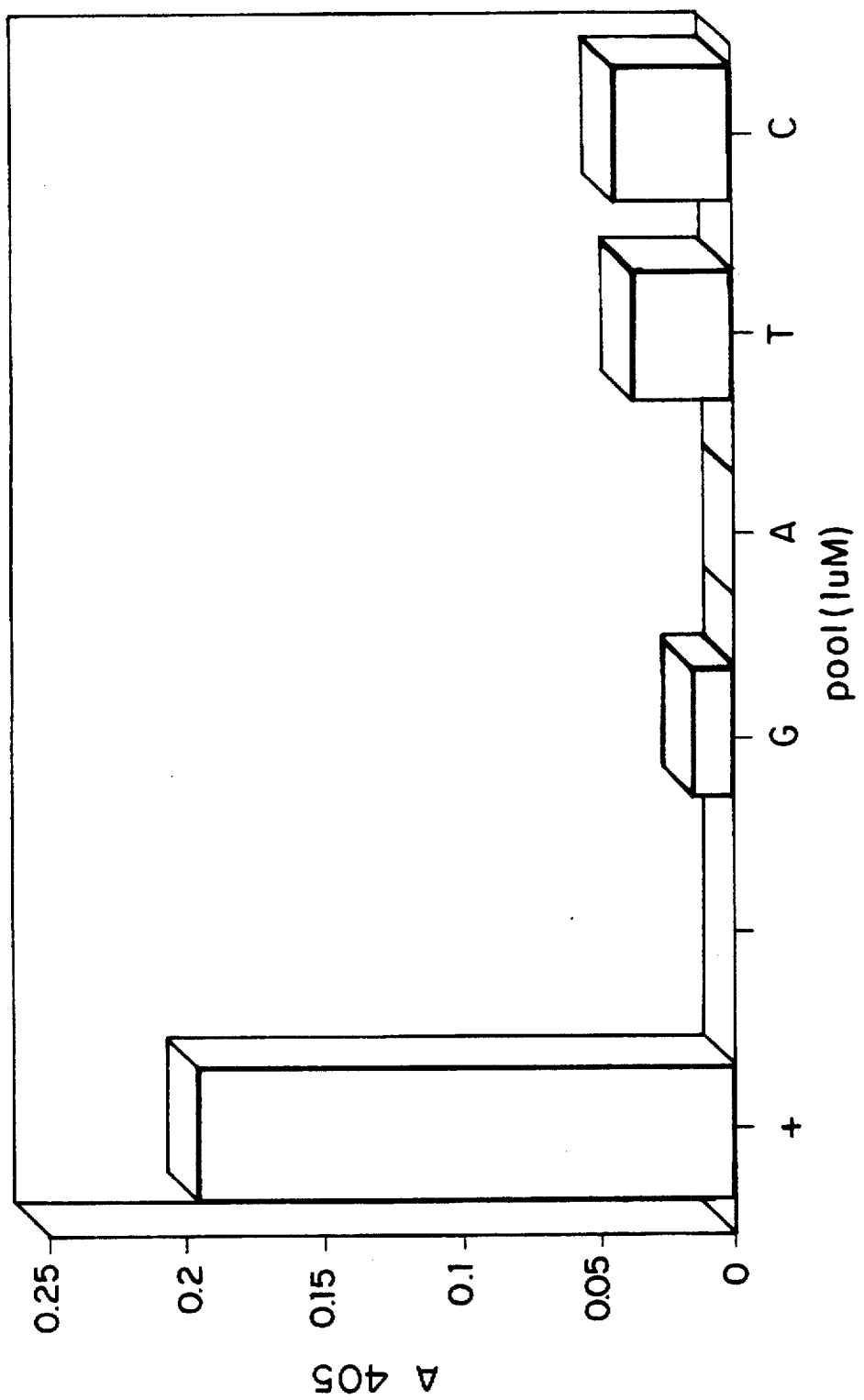
FIG. 1 is a schematic representation showing binding affinity of four sets of phosphorothioate oligonucleotides for the transcription factor c-rel. The phosphorothioate oligonucleotide set having the sequence TNNNCNNNT-B had the greatest activity, indicated by amount of binding. The phosphorothioate oligonucleotide set having the sequence TNNNANNNT-B had the least activity, exhibited little to no binding of c-rel.

Combinatorial strategies offer the potential to generate and screen extremely large numbers of compounds and to identify individual molecules with a desired binding specificity or pharmacological activity. This invention is directed to substantially non-enzymatic methods of determining oligomers which are specifically active for transcription factors and other target molecules.

Methods of the present invention are useful for the determination of oligomers which have specific activity for transcription factors from a pool of primarily randomly assembled subunits. Said methods involve repeated syntheses of increasingly simplified sets of oligomers coupled with selection procedures for determining the oligomer set having the greatest activity in an assay for desired activity.

Simplification of the pool occurs because, with each additional step of the methods, at least one additional position in the oligomer is determined. As a result, the possible number of different oligomer molecules in the pool decreases sequentially with the number of random positions remaining in the oligomer.

Freedom from the use of enzymes allows the application of these methods to any molecules which can be oligomerized in a controlled fashion.

In one embodiment of the present invention, methods for making oligonucleotides having specific activity for a transcription factor are provided. These methods involve preparing a group comprising a plurality of sets of oligonucleotides, each oligonucleotide comprising at least four base units, by defining a common position in the oligonucleotides of the sets and synthesizing said sets of oligonucleotides such that each set has a different base unit in said common position and the base units which are not in the common position are randomized. Each of the sets are then assayed for activity against the transcription factor and the set having the greatest activity for the transcription factor is selected. In other embodiments of the present invention each group of oligonucleotides may be subfractionated to provide subfractions of the sets of oligonucleotides. Each subfraction may be assayed against the transcription factor and the set from which the subfraction having the highest activity was derived is selected.

These methods further comprise preparing a further group comprising a plurality of sets of oligonucleotides, each of the sets having in the previously defined common position the base unit appearing in the previously defined common position in the previously selected set. Each of said further group of sets has a different base unit in an additional, defined common position. The base units in positions of the oligonucleotides which are not in a common position are randomized. In other embodiments of the invention this group may subfractionated to provide subfractions of the sets of oligonucleotides.

Each of said sets or subfractions of sets may be assayed for activity for the transcription factor and the set having the highest activity, or the set from which the subfraction having the highest activity was derived, is selected. The preceding steps may be performed iteratively.

Methods of determining an oligonucleotide cassette having specific activity for a transcription factor are also provided by the present invention. These methods involve preparing a group comprising a plurality of sets of oligonucleotides, each oligonucleotide comprising at least four base units, by defining a common position in the oligonucleotides of the sets and synthesizing said sets of oligonucleotides such that each set has a different base unit in said common position and the base units which are not in the common position are randomized. Each of the sets are then assayed for activity for a transcription factor and the set having the greatest activity for the transcription factor is selected. Thereafter, a further group is prepared comprising a plurality of sets of oligonucleotides, each of the sets having in the previously defined common position the base unit appearing in the previously defined common position in the previously selected set. Each of said further group of sets has a different base unit in an additional defined common position. The base units in positions of the oligonucleotides which are not in a defined common position are randomized. Each set of said further group is assayed for specific activity for the transcription factor and the set having the highest activity is selected. The preceding steps are performed iteratively to provide an oligonucleotide cassette having each position defined.

In other embodiments of the invention, methods for determining an oligonucleotide having specific activity for a transcription factor are provided. Such methods comprise preparing a group comprising a plurality of sets of oligonucleotides, each of the oligonucleotides comprises at least one oligonucleotide cassette and at least one flanking region. A common position is defined in a flanking region of the oligonucleotides of the sets and the sets of oligonucleotides are synthesized such that each set has a different base unit in said common position and the base units which are not in the common position are randomized. Each of the sets are then assayed for activity for a transcription factor and the set having the greatest activity for the transcription factor is selected.

These methods also may comprise preparing a further group comprising a plurality of sets of oligonucleotides, each of the sets having in the previously defined common position the base unit appearing in the previously defined common position in the previously selected set. Each of said further group of sets having a different base unit in an additional, defined common position in the flanking region. The base units in positions of the oligonucleotides which are not in a common position in the flanking region are randomized. Each of the sets of oligonucleotides are assayed for specific activity for the transcription factor and the set having the highest activity is selected. The preceding steps may be and preferably are performed iteratively.

In still other embodiments of the present invention are provided methods for determining an oligonucleotide having specific activity for a transcription factor comprising preparing a group comprising a plurality of sets of oligonucleotides. Each oligonucleotide comprises at least four nucleotide units and a common position is defined in the oligonucleotides of the sets. Said sets of oligonucleotides are synthesized such that each set has a different base unit in said common position, the base units which are not in said common position being randomized. The oligonucleotides of the sets of oligonucleotides are modified with linker moieties for attaching the oligonucleotide to a solid support. Thereafter the sets of oligonucleotides are each incubated with the transcription factor under binding conditions to form oligonucleotide-transcription factor complexes, and the oligonucleotides are attached to a solid support via the linker moiety. Bound and unbound transcription factor molecules are separated and binding of the transcription factor to each set of oligonucleotides is detected wherein the greatest binding is indicative of highest activity. The set having highest activity is selected.

In accordance with other embodiments of the present invention, oligonucleotide sets are prepared, and oligonucleotides of each set of oligonucleotides are detectably labeled. The transcription factor is modified with a linker moiety for attaching the transcription factor to a solid support and incubated with each of said sets of oligonucleotides under binding conditions to form oligonucleotide-transcription factor complexes. The transcription factor is attached to a solid support via the linker moiety and bound from unbound oligonucleotide is separated. The binding of each oligonucleotide set to the transcription factor is detected wherein greatest binding is indicative of highest activity. The set having highest activity is selected.

In still other embodiments of the present invention, oligonucleotide sets are prepared and the transcription factor is modified with a linker moiety for attaching the transcription factor to a solid support. The transcription factor is incubated with each of the sets of oligonucleotides under binding conditions to form oligonucleotide-transcription factor complexes. A competitor is added under binding conditions to form transcription factor-competitor complexes. The transcription factor is attached to a solid support via the linker moiety and bound and unbound competitor are separated. Binding of the competitor is detected wherein lowest binding is indicative of highest oligonucleotide activity. The set having the highest oligonucleotide activity is selected.

In yet other embodiments of the present invention, oligonucleotide sets are prepared and a competitor is modified with a linker moiety for attaching the competitor to a solid support. Each of the oligonucleotide sets are incubated with the transcription factor under binding conditions to form oligonucleotide-transcription factor complexes. The competitor is added under binding conditions to form transcription factor-competitor complexes. The competitor is attached to a solid support via the linker moiety and bound and unbound transcription factor molecules are separated. Binding of the transcription factor to the competitor is detected wherein lowest binding is indicative of highest oligonucleotide activity. The set having the highest activity is selected.

In other embodiments of the present invention oligonucleotide sets are prepared and a first competitor is modified with a linker moiety for attaching the first competitor to a solid support. The transcription factor and the first competitor are incubated under binding conditions to form transcription factor-competitor complexes. Each of the oligonucleotide sets are incubated with the transcription factor-competitor complexes under binding conditions to form oligonucleotide-transcription factor-competitor complexes. A second competitor is added under binding conditions to form further complexes. The first competitor is attached to a solid support via the linker moiety and bound from unbound second competitor is separated. Binding of the second competitor to the transcription factor is detected wherein lowest binding is indicative of highest oligonucleotide activity. The set having the highest activity is selected.

In still further embodiments of the present invention oligonucleotide sets are prepared and the oligonucleotides of the sets are detectably labeled. A first competitor is modified with a linker moiety for attaching the first competitor to a solid support and incubated with the transcription factor under binding conditions to form transcription factor-competitor complexes. Each of the sets of oligonucleotides are incubated with the transcription factor-competitor complexes under binding conditions to form oligonucleotide-transcription factor-competitor complexes. A second competitor is added under binding conditions to form further complexes and the first competitor is attached to a solid support via the linker moiety. Bound from unbound oligonucleotide is separated and binding of the oligonucleotide to the transcription factor is detected wherein highest binding is indicative of highest oligonucleotide activity. The set having the highest activity is selected.

DETAILED DESCRIPTION OF THE INVENTION

The present invention is directed to non-enzymatic methods for determining oligomers which have specific binding activity for a transcription factor. In one embodiment of the present invention methods of determining oligonucleotides having specific binding affinity for a transcription factor are provided.

In the context of the present invention an oligomer is a string of units linked together by chemically similar covalent linkages. Nucleic acids linked together via phosphodiester bonds to form polynucleotides, amino acids linked together via peptide bonds to form polypeptides and monosaccharides linked together via glycosidic linkages to form polysaccharides are examples of naturally occurring oligomers. Also encompassed by the term "oligomer" includes two or more oligomer species linked together. For example, polypeptides and polysaccharides may be linked together to form glycoproteins and lipids and polysaccharides may be linked together to form glycolipids.

In the context of this invention, the term "oligonucleotide" refers to a polynucleotide formed from naturally occurring bases and furanosyl groups joined by native phosphodiester bonds. This term effectively refers to naturally occurring species or synthetic species formed from naturally occurring subunits or their close homologs. The term "oligonucleotide" may also refer to moieties which have portions similar to naturally occurring oligonucleotides but which have non-naturally occurring portions. Thus, oligonucleotides may have altered sugar moieties or inter-sugar linkages. Exemplary among these are the phosphorothioate and other sulfur-containing species which are known for use in the art. In accordance with some preferred embodiments, at least some of the phosphodiester bonds of the oligonucleotide have been substituted with a structure which functions to enhance the stability of the oligonucleotide or the ability of the oligonucleotide to penetrate into the region of cells where the viral RNA is located. It is preferred that such substitutions comprise phosphorothioate bonds, phosphotriesters, methyl phosphonate bonds, short chain alkyl or cycloalkyl structures or short chain heteroatomic or heterocyclic structures. Most preferred are $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ structures where phosphodiester is O—P—O—$CH_2$). Methods of preparing such oligonucleotides are well known in the art and may be synthesized by modification of procedures such as described in Goodchild, Bioconjugate Chemistry, 1990, 1:165–187; Ulhmann and Peyman, Chemical Reviews, 1990, 90, 543–584; and PCT US91/05713 filed Aug. 12, 1991; incorporated by reference herein in their entirety. Also preferred are morpholino structures. Summerton, J. E. and Weller, D. D., U.S. Pat. No. 5,034,506 issued Jul. 23, 1991. In other preferred embodiments, such as the protein-nucleic acid (PNA) backbone, the phosphodiester backbone of the oligonucleotide may be replace with a polyamide backbone, the bases being bound directly or indirectly to the aza nitrogen atoms of the polyamide backbone. P. E. Nielsen, et al., Science 1991 254 1497. In accordance with other preferred embodiments, the phosphodiester bonds are substituted with other structures which are, at once, substantially non-ionic and non-chiral, or with structures which are chiral and enantiomerically specific. Persons of ordinary skill in the art will be able to select other linkages for use in practice of the invention.

Oligonucleotides may also include species which include at least some modified base forms. Thus, purines and pyrimidines other than those normally found in nature may be so employed such as disclosed in PCT/US91/04681 filed Jul. 1, 1991, incorporated by reference herein in its entirety. Similarly, modifications on the furanosyl portion of the nucleotide subunits may also be effected, as long as the essential tenets of this invention are adhered to. Examples of such modifications are 2'-O-alkyl- and 2'-halogen-substituted nucleotides such as described in Uhlmann and Peyman, Chemical Reviews, 1990, 90, 543–584. Some specific examples of modifications at the 2' position of sugar moieties which are useful in the present invention are OH, SH, $SCH_3$, F, OCN, $O(CH_2)_nNH_2$, $O(CH_2)_nCH_3$ where n is from 1 to about 10; $C_1$ to $C_{10}$ lower alkyl, substituted lower alkyl, alkaryl or aralkyl; Cl, Br, CN, $CF_3$, $OCF_3$, O—, S—, or N— alkyl; O—, S—, or N—alkenyl; $SOCH_3$, $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a conjugate; a reporter group; an intercalator; a group for improving the pharmacokinetic properties of an oligonucleotide; or a group for improving the pharmacodynamic properties of an oligonucleotide and other substituents having similar properties. Sugar mimetics such as cyclobutyls may also be used in place of the pentofuranosyl group. Oligonucleotides may also comprise other modifications consistent with the spirit of this invention. Such oligonucleotides are best described as being functionally interchangeable with yet structurally distinct from natural oligonucleotides. All such oligonucleotides are comprehended by this invention so long as they effectively function as subunits in the oligonucleotide.

The methods of the present invention are useful to determine oligomers which are specifically active for a transcription factor. In the context of the present invention determine refers to concurrent identification of the sequence of an oligomer and the binding activity of the oligomer for a transcription factor. In some instances, neither the oligomer sequence nor its specific activity is known prior to performance of methods of the present invention. In other cases, while a particular oligomer sequence may be known, those skilled in the art may not recognize its activity for a particular transcription factor. In still other cases, activity of a known sequence for a particular transcription factor may be optimized.

Oligomers of the present invention are assayed for specific binding activity for a transcription factor. As used herein, binding affinity refers to the ability of the oligomer to bind to a transcription factor via hydrogen bonds, van der Waals interactions, hydrophobic interactions, or otherwise. For example an oligomer may bind to a "leucine zipper" transcription factor or a helix-loop-helix transcription factor via positively charged amino acids in one region of the transcription factor.

Transcription factors, as the term is used herein, refers to DNA- or RNA-binding proteins which regulate the expression of genes. HIV tat and c-rel are examples of transcription factors which regulate the expression of genes. Also encompassed by the term are DNA and RNA binding proteins which are not strictly considered transcription factors, but which are known to be involved in cell proliferation. These transcription factors include c-myc, fos, and jun. Methods of the present invention are particularly suitable for use with transcription factor as target molecules since transcription factors generally occur in very small cellular quantities. Methods of the present invention require relatively small amounts of transcription factor which may, but need not, be purified.

Of course, methods of the present invention may also be useful to determine oligomers having specific binding affinity for other target molecules. Target molecules of the present invention may include any of a variety of biologically significant molecules. Target molecules may be nucleic acid strands such as significant regions of DNA or RNA. Target molecules may also be carbohydrates, glycoproteins or other proteins. In some preferred embodiments of the present invention, said target molecule is a protein such as an immunoglobulin, receptor, receptor binding ligand, antigen or enzyme and more specifically may be a phospholipase, tumor necrosis factor, endotoxin, interleukin, plasminogen activator, protein kinase, cell adhesion molecule, lipoxygenase, hydrolase or transacylase. In other preferred embodiments of the present invention said target molecules may be important regions of the human immunodeficiency virus, Candida, herpes viruses, papillomaviruses, cytomegalovirus, rhinoviruses, hepatitises, or influenza viruses. In yet other preferred embodiments of the present invention said target molecules may be regions of an oncogene. In still further preferred embodiments of the present invention said target molecule is ras 47-mer stem loop RNA, the TAR element of human immunodeficiency virus or the gag-pol stem loop of human immunodeficiency virus (HIV). Still other targets may induce cellular activity. For example, a target may induce interferon.

In some aspects of the present invention, the transcription factor need not be purified, but may be present, for example, in a crude cell lysate containing the transcription factor, serum or extract. Of course, purified transcription factor is also useful in some aspects of the invention. In still other embodiments of the present invention, synthetically prepared transcription factor may be useful. The transcription factor may also be modified, such as by biotinylation or radiolabeling. For example, synthetically prepared transcription factor may incorporate one or more biotin molecules during synthesis or may be modified post-synthesis.

In the present invention, a group of sets of random oligomers is prepared. Oligomers may be prepared by procedures known to those skilled in the art. Generally, oligonucleotides, polypeptides, polysaccharides, glycoproteins and glycolipids may be prepared by solid state synthesis or by other means known to those skilled in the art. For example, oligonucleotides may be prepared using standard phosphoramidite chemistry. In some embodiments of the present invention oligomer groups may further be labeled, such as by radiolabeling or fluorescent labeling. For example, an oligonucleotide group may be labeled at the 5' termini of the oligonucleotides using $[\gamma\text{-}^{32}P]$ ATP and T4 polynucleotide kinase. Labeled oligomer groups may be useful in a number of assays which can not be performed using unlabeled oligomer groups.

Oligomers of each set may be of predetermined length. It is preferred that such oligomers be from about 4 to about 50 units in length. It is more preferred that such oligomers be from 4 to about 40 units in length. It is also preferred for some embodiments of the present invention that less than about 10 units of an oligomer are randomized. In some cases, it may be desirable to provide an oligomer which initially comprises 6, 7, or 8 random units.

In some embodiments of the present invention, the length of said oligomer need not be constant throughout the procedure. For example, an 8-mer may be assayed to determined the sequence having highest binding affinity for a transcription factor. Subsequently, the 8-mer may be extended and tested as a 15-mer to determine the 15-mer sequence having the highest binding affinity for the transcription factor.

Groups of the present invention are made up of a plurality of sets which may remain constant throughout the procedure. From about three to about twenty sets can make up each group. In one preferred embodiment of the present invention four sets make up each group. In another embodiment of the present invention twenty sets make up each group. Alternatively, three sets may make up each group.

The number of sets that make up each group is dependent upon the number of possible distinct chemically similar units which exist for any one species of molecule. For example, an oligonucleotide group may be comprised of four sets since there are four similar units making up the nucleic acid species, i.e. guanine, adenine, cytosine, thymine or adenine, guanine, cytosine and uracil. Alternatively, an oligonucleotide group may be comprised of more than four sets representing for example, the four commonly occurring bases and additional modified bases. Twenty sets may make up a polypeptide group, representing the twenty commonly occurring amino acids, lysine, arginine, histidine, aspartic acid, glutamic acid, glycine, asparagine, glutamine, cysteine, serine, threonine, tyrosine, alanine, valine, leucine, isoleucine, proline, phenylalanine, methionine and tryptophan. Greater than twenty sets may also make up a polypeptide group if uncommon or modified amino acids are included in the assay. Subgroups of basic units may also determine the number of sets in any one group. For example, in procedures to determine a particular polypeptide, sets may represent acidic, basic and neutral amino acid units, i.e. three sets. The number of sets in groups in any one procedure need not remain constant throughout, but may fluctuate. For example, in a one group there may be three sets representing three types of polypeptides and in a next group there may be twenty sets representing each commonly occurring amino acid.

The use of additional units such as nucleotide or amino acid analogs may be preferred in some instances where it is desirable to increase the complexity of the group of oligomers. The complexity of a group may be calculated by the formula $P \times P^N$ where P is the number of different units used and N is the number of positions in an oligomer which are randomized. The complexity of a set (Q) is represented by the formula $P^N$. Table 1 illustrates the change in group complexity as a result of the increase in the number of analogs used. Of course, the number of different units used also determines the number of sets prepared.

TABLE 1

Group Structure = NNN X NNN

| Number of different analogs used (P) | Complexity of each set (Q) (P$^6$) | Total Group Complexity (P · P$^6$) |
|---|---|---|
| 4 | $4^6$ = 4096 | 4 × 4096 = 16,384 |
| 5 | $5^6$ = 15,625 | 5 × 15,625 = 78,125 |
| 6 | $6^6$ = 46,656 | 6 × 46,656 = 279,936 |
| 7 | $7^6$ = 117,649 | 7 × 117,649 = 823,543 |
| 8 | $8^6$ = 262,144 | 8 × 262,144 = 2,097,152 |
| 9 | $9^6$ = 531,441 | 9 × 531,441 = 4,782,969 |
| 10 | $10^6$ = 1,000,000 | 10 × 1,000,000 = 10,000,000 |

Each of the sets in a group has a different unit in a common position of said oligomer. For example, in determining an oligonucleotide, only one of four sets will contain an adenine in a common position, only one set will contain a guanine in a common position, etc. The remaining positions in each set of oligonucleotides are comprised of any combination of random basic units.

In further embodiments of the present invention, common positions are comprised of multiple oligomer positions. For example, for a 9-mer, one common position may be the third position of the 9-mer, or the common position may be comprised of the third position and the fourth position of the 9-mer.

In some aspects of the invention, it may be desirable to begin a procedure by unrandomizing central regions of an oligomer as opposed to end regions, such as the 3' or 5' regions of an oligonucleotide or the carboxy or amino terminal regions of a polypeptide, since it has been found that in some cases defining a central position had a greater affect on specific activity of an oligomer than did defining an end region during a similar stage of a determination. For example, in Example 8 an attempt to fix a 3' position did not yield results that distinguished the sets, whereas a position in the center of the oligomer was fixed to yield results which were detectable.

Furthermore, there is a complexity limit to the detectability of activity (signal-to-noise), especially in oligomers having a high percentage of unrandomized positions. It is likely that with largely unstructured, conformationally dynamic oligomers, a plethora of relatively weak specific activity towards many target molecules will result. As discussed, this may be improved by increasing the number of units used. An additional method of increasing specific activity of a group of oligomers is to constrain the oligomer sterically. For example, an oligonucleotide may be sterically constrained by providing complementary ends at the 3' and 5' termini of the region of interest, which region comprises randomized positions. The complementary ends will hybridize to form a secondary structure.

The detectable specific activity may also be enhanced by the determination and/or use of an oligomer "cassette". An oligomer cassette is a oligomer for which a sequence has been determined. The cassette may be comprised of a sequence of known significance, or may be determined such as by the procedures of the present invention. As used herein an oligonucleotide cassette is a defined oligonucleotide sequence. In some embodiments of the present invention an oligomer may comprise at least one oligomer cassette and at least one flanking region of unrandomized positions. In other embodiments of the present invention an oligomer may be comprised of more than one cassette wherein each cassette is flanked by at least one region of randomized positions. For example, a oligonucleotide cassette of known sequence may be flanked at the 3' terminus, the 5' terminus, or both the 3' and 5' termini.

In some embodiments of the present invention it may also be desirable to subfractionate a group of oligomers to provide subfractions of the sets of oligomers, thus delimiting the degree of complexity that is assayed at one time. This both diminishes the amount of total material that must be used in a determination in order to have sufficient representation of all individual sequences and it also enhances the signal to noise ratio of the assay by starting with oligomer sets enriched in the most active sequences. Any physical-chemical or functional characteristic, combined with an appropriate separation modality may be used to empirically subfractionate a group, thereby resulting in (or deriving) numerous distinct subfractions of diverse character, and diminished complexity. It is theorized that if a particular fit sequence or sequences exist within the original group for a particular transcription factor, it will be found enriched in a limited number of the reduced complexity subfractions.

One skilled in the art would be apprised of the broad selection of appropriate selection modalities which are available. The strategy followed will of course depend upon the properties of the elements of the oligomer group. It will further be appreciated by one skilled in the art that as the number of group elements increases and the structural and chemical diversity enlarges, there will be a greater selection of separation strategies leading to increased subfractionation capacity. By way of example, it is envisioned that novel oligomers may be resolved into subfractions by any one or a combination of size, positive or negative charge, hydrophobicity and affinity interactions. Many chromatographic and analytical instrumental methods are known to those skilled in the art which may be effectively applied to the separation strategies encompassed herein.

In some embodiments of the invention each set of oligomers is assayed for desired activity. In other embodiments of the present invention, identical empirical assays of subfractions of oligomer sets described above are performed in order to identify those subfractions having the strongest activity as indicated by a strong signal to noise ratio. The set having the highest activity or the set from which the subfraction having the highest activity is derived is selected and further unrandomization may be performed if desired.

Specific activity may be detected by methods known to those skilled in the art. Appropriate assays will be apparent to one skilled in the art and oligomer concentration, target molecule concentration, salt concentration, temperature, buffer and buffer concentration may be altered to optimize a particular system. In some preferred embodiments of the present invention, binding conditions simulate physiological conditions. In other preferred embodiments of the present invention binding occurs in a buffer of from about 80 mM to about 110 mM sodium chloride and from about 10 to about 15 mM magnesium chloride. Oligomers may also generally be assayed for catalytic or enzymatic activity.

Gel shift assays may be used to visualize binding of an oligomer to a transcription factor. In accordance with methods of the present invention, radiolabelled transcription factor bound to oligomer of the present invention may be run on a gel such as a polyacrylamide gel. Bound transcription factor has less mobility than unbound transcription factor, and therefore will not migrate as far on the gel. The radioactive label allows visualization of the "shift" in mobility by standard procedures for example, by means of X-ray radiography or by using a phosphorimager (Molecular Dynamics). In other embodiments of the present invention a gel shift assay may be performed wherein an unlabeled transcription factor may be bound to radiolabelled oligomer.

Radiolabeled oligomer may also be useful for the streptavidin capture of a biotin-transcription factor bound to an oligomer. For example, a transcription factor may be biotinylated prior to incubation with radioactively labeled random oligomer sets. Such biotinylation can be performed by those skilled in the art using well know reagents and procedures. Each set is thereafter incubated with the transcription factor under identical conditions and the transcription factor is captured on streptavidin-coated beads. Alternatively, the transcription factor may be captured prior to incubation with the oligomer. Consequently any oligomer which bound to the transcription factor will also be captured. Streptavidin-coated beads are available commercially such as for example, streptavidin-coated manganese particles available from Promega. The beads are washed and the reaction may be reequilibrated to further enrich the "winning" sequence. The percent of oligomers from each set which bound is determined by the amount of radioactivity remaining after wash. Measuring radioactivity in a sample may be performed by a number of methods known in the art. For example, the amount of radioactivity may be determined directly by counting each sample, using for example a scintillation counter. Samples may also be run on a polyacrylamide gel, the gel may be placed under x-ray film and a densitometric reading of the autoradiogram may be taken.

Alternatively, a competitor may be co-incubated with transcription factor and oligomer sets to determine which oligomer set best competes for a binding site against a molecule known to bind to the transcription factor. A competitor, in the context of this invention, is a molecule which is known to recognize the transcription factor. The competitor may be, for example, a double or single stranded oligonucleotide. The competitor may, in other embodiments of the present invention, be a protein known to bind to the transcription factor. For example, a truncated version of the TAR hairpin loop naturally recognizes the HIV tat protein and may compete with oligomers of the present invention, preventing binding of the oligomer to the HIV tat transcription factor. A DNA myc binding site may compete with oligomers of the present invention for the myc nuclear protein and the NF-kB binding site may compete with oligomers of the present invention for the rel transcription factor.

A "capture" assay may also be performed without the use of radioactivity. For example, each set of random oligomers may be prepared with a linker moiety. In accordance with methods of the present invention the linker moiety is a moiety which is useful for attaching the oligomer, and anything appended thereto, to a solid support by chemical bond, or otherwise. For example, well known linker moieties include chemical handles such as biotin and polyT. Such linker moieties may be incorporated during synthesis of the oligomer, or may be incorporated following synthesis. Thereafter, each set of oligomers is incubated with the transcription factor under identical conditions and the oligomers are attached to a solid support via the linker moiety. Alternatively, the transcription factor and oligomer sets are incubated following attachment of the oligomers to a solid support. Thus, in one preferred embodiment, biotin-labeled oligomers may be captured on a streptavidin-coated solid support such as streptavidin-coated beads or streptavidin-coated plates. In another preferred embodiment, polyT-labeled oligomer may be attached to a polyA-labeled solid phase. Consequently, any transcription factor which has bound to oligomers will also be attached. The solid support is washed and the reaction may be reequilibrated to further enrich the "winning" sequence. Thereafter binding of the transcription factor is detected such as by the use of an antibody which is specific for the transcription factor. The antibody may detect and quantitate the set which bound the most transcription factor either by attached reporter or a secondary antibody containing a reporter. In such an assay, the oligomer set having the most binding is the "winner" set.

In still other embodiments a competitor may be co-incubated with transcription factor and oligomer sets to determine which oligomer set best competes for a binding site against a molecule known to bind to the transcription factor.

Another assay which may be useful for the detection of oligomer binding is a "competition" assay. This assay selects for molecules which bind to a transcription factor specifically at the site that the protein naturally binds a molecule of interest (a competitor). Thus, this assay selects for a competitive inhibitor. In accordance with this assay, each set of oligomers may be incubated with the transcription factor under binding conditions. To this incubating mixture is then added a competitor. A competitor, in the context of this invention, is a molecule which is known to recognize the transcription factor. The competitor may be, for example, a double or single stranded oligonucleotide. The competitor may, in other embodiments of the present invention, be a protein or peptide known to bind to the transcription factor. The competitor further comprises a linker moiety which can be used to attach the competitor to a solid support. For example, the competitor may be modified or synthesized with a chemical handle such as biotin or polyT. The competitors are attached to a solid support via the linker moiety either before or after incubation with the transcription factor and oligomer sets. Thus, in one preferred embodiment, biotin-labeled competitor may be attached to a streptavidin-coated solid support such as streptavidin-coated beads or streptavidin-coated plates. In another preferred embodiment, poly T-labeled competitors may be captured on a poly A-labeled solid support. Consequently any transcription factor which is bound to the competitor will also be bound while transcription factor bound to oligomers will not be bound. Thereafter the solid support is washed. The percent of binding of the transcription factor to the competitor is determined by the use of an antibody which is specific for the transcription factor. The antibody may detect and quantitate the set which bound the most transcription factor either by attached reporter or a secondary antibody containing a reporter. In "competition" assays, oligomer sets which bind the transcription factor prevent binding to the competitor which is also present in the assay. Since only the competitor can be attached to the solid support, only transcription factor molecules which are able to bind the competitor will remain on the solid support after washing. Therefore, oligomer sets which retain or bind more transcription factor should lower the amount of transcription factor available to bind the competitor and therefore lower the overall signal in a "competition" assay.

Still another assay which selects for molecules which bind to a transcription factor specifically at the site that the protein naturally binds a molecule of interest (a competitor) is the "heterodimer targeting" assay. This assay also selects for a competitive inhibitor. In accordance with this assay, the transcription factor is incubated with a first competitor which functions to attach the transcription factor to a solid support. In some embodiments of the present invention, such a first competitor may be a double or single stranded oligonucleotide known to recognize and bind to the transcription factor. The first competitor further comprises a linker moiety which can be used to attach the first competitor to a solid support. For example, the first competitor may be modified or synthesized with a chemical handle such as biotin or polyT. The first competitor is attached to a solid support via the linker moiety. Thus, in one preferred embodiment, biotin-labeled first competitor may be captured on a streptavidin-coated solid support such as streptavidin-coated beads or streptavidin-coated plates. In another preferred embodiment, poly T labeled first competitors may be attached to a poly A labeled solid support. In still other embodiments of the present invention, the transcription factor is directly attached to the solid support via a linker moiety such a biotin or polyT as described above. Following attachment of the transcription factor. Each set of oligomers may be incubated with a sample of the transcription factor under binding conditions. Thereafter, a second competitor is added. Alternatively, attachment may follow incubation. The solid support is washed and presence of the second competitor is detected by the use of an antibody which is specific for the second competitor. The antibody may detect and quantitate the oligomer set which bound the most transcription factor either by attached reporter or a secondary antibody containing a reporter. The set which competes most effectively with the natural recognition site of the competitor to the transcription factor will produce the lowest signal.

In further embodiments of the present invention further groups of sets are prepared. Each of said further groups have a selected number of sets of oligomers. Sets of further groups have in a previously defined common position, units appearing in the previously defined common position in previously selected set. Each set of the further sets has a different unit in an additional defined common position. The units in the positions of the oligomer that are not in a common position are randomized.

For example, in one group, the previously selected set may be comprised of an adenine in the previously defined common position. A further group may retain said adenine in said previously defined common position, and at another defined common position each set in said further group may be comprised of a different unit, either adenine, guanine, thymine or cytosine. The units in the positions of the oligomer that are not in a common position are randomized.

In further embodiments of the present invention, common positions are comprised of multiple oligomer positions as described above. For example, for a 9-mer, the one common position may be the third position of the 9-mer, or the common position may be comprised of the third position and the fourth position of the 9-mer.

Procedures useful for increasing the complexity of an oligomer group, and/or increasing specific activity of an oligomer described previously are equally applicable to said further groups. Thus, oligomer groups may be comprised of multiple units, may be sterically constrained and may be subfractionated prior to assaying for specific activity. Furthermore, oligomers of further groups may comprise one or more cassettes.

Sets are again assayed for desired activity. The steps described above may be performed iteratively.

The following examples are illustrative, but not limiting of the invention.

EXAMPLE 1

Synthesis of DNA Oligonucleotides

Unmodified DNA oligonucleotides are synthesized on an automated DNA synthesizer (Applied Biosystems model 380B) using standard phosphoramidite chemistry with oxidation by iodine. β-cyanoethyldiisopropyl phosphoramidites may be purchased from Applied Biosystems (Foster City, Calif.).

EXAMPLE 2

Synthesis of RNA Oligonucleotides

Unmodified RNA oligonucleotides having random base sequences were synthesized on an automated DNA synthesizer (Applied Biosystems model 380B) using modified standard phosphoramidite chemistry synthesis with oxidation by iodine. The standard synthesis was modified by increasing the wait step after the pulse delivery of tetrazole to 900 seconds. β-cyanoethyldiisopropyl phosphoramidites were purchased from Applied Biosystems (Foster City, Calif.). The bases were deprotected by incubation in methanolic ammonia overnight. Following base deprotection, the oligonucleotides were dried in vacuo. The t-butyldimethylsilyl protecting the 2' hydroxyl was removed by incubating the oligonucleotide in 1M tetrabutylammoniumfluoride in tetrahydrofuran overnight. The RNA oligonucleotides were further purified on $C_{18}$ Sep-Pak cartridges (Waters, Division of Millipore Corp., Milford, Mass.) and ethanol precipitated.

EXAMPLE 3

Synthesis of Phosphorothioate Oligonucleotides

Phosphorothioate oligonucleotides represent a class of oligonucleotide analog that is substantially nuclease resistant. Phosphorothioate RNA oligonucleotides and phosphorothioate DNA oligonucleotides were synthesized according to the procedure set forth in Examples 1 and 2 respectively, replacing the standard oxidation bottle by a 0.2M solution of 3H-1,2-benzodithiole-3-one 1,1-dioxide in acetonitrile for stepwise thiation of phosphite linkages. The thiation cycle wait step was increased to 68 seconds and is followed by the capping step.

EXAMPLE 4

Synthesis of 2'-O-alkyl Phosphorothioate Oligonucleotides

2'-O-methyl phosphorothioate oligonucleotides were synthesized according to the procedures set forth in Example 3 substituting 2'-O-methyl β-cyanoethyldiisopropyl phosphoramidites (Chemgenes, Needham, Mass.) for standard phosphoramidites and increasing the wait cycle after the pulse delivery of tetrazole and base to 360 seconds. Similarly, 2'-O-propyl, 2'-O-phenyl and 2'-O-nonyl phosphorothioate oligonucleotides may be prepared by slight modifications of this procedure.

EXAMPLE 5

Preparation of Pyrene Oligonucleotide Analogs

Oligonucleotides were prepared by incorporating 2' aminopentoxyadenosine at desired sites. The oligonucleotides were dissolved in 0.2M $NaHCO_3$ buffer and treated with 50 fold excess of N-hydroxysuccinimide ester of pyrene-1-butyric acid dissolved in dimethylformamide. The resultant mixture is incubated at 37° C. for 4–5 hours and the conjugate is purified by reverse phase HPLC followed by desalting in a G-25 Sephadex column.

EXAMPLE 6

Synthesis of Oligonucleotide Having Randomized Positions

Four columns of the DNA synthesizer were packed with a mixture containing an equal amount of adenosine(A)-, cytidine(C)-, guanosine(G)- and uracil(U)-controlled pore glass (CPG, Chemgenes, Needham, Mass.). At coupling steps where a given nucleotide base was desired, the defined phosphoramidite was delivered to each column. At each "random" coupling step, an equimolar mixture of all four phosphoramidites was delivered to each column.

EXAMPLE 7

Preparation of Radiolabeled Groups

Oligonucleotide groups prepared in accordance with Example 1 through 6 may be radiolabeled using [γ-$^{32}$P] ATP and T4 polynucleotide kinase as described in Maniatis, et al. "Molecular Cloning: A Laboratory Manual" (Cold Spring Harbor, N.Y.).

EXAMPLE 8

Effect of Site of Unrandomization on Activity

Twenty-four sets of phosphorothioate oligonucleotides were prepared in accordance with Examples 3 and 6 as set forth in Table 2.

TABLE 2

| Set 1 | ANNNNN | Set 13 | NNNANN |
|---|---|---|---|
| Set 2 | CNNNNN | Set 14 | NNNCNN |
| Set 3 | GNNNNN | Set 15 | NNNGNN |
| Set 4 | TNNNNN | Set 16 | NNNTNN |
| Set 5 | NANNNN | Set 17 | NNNNAN |
| Set 6 | NCNNNN | Set 18 | NNNNCN |
| Set 7 | NGNNNN | Set 19 | NNNNGN |
| Set 8 | NTNNNN | Set 20 | NNNNTN |
| Set 9 | NNANNN | Set 21 | NNNNNA |
| Set 10 | NNCNNN | Set 22 | NNNNNC |
| Set 11 | NNGNNN | Set 23 | NNNNNG |
| Set 12 | NNTNNN | Set 24 | NNNNNT |

Each of the sets is tested for activity against a target molecule to determine which order of unrandomization gives the highest initial specific activity.

EXAMPLE 9

Preparation of a Biotin Oligonucleotide Group

An oligonucleotide group having the sequence TNNNXNNNTB, wherein N is any of A, G, C, or U, X is one of A, G, C and U and B is biotin, is prepared in accordance with Examples 3 and 6. Biotin may be incorporated at the 3' or 5' end of the oligonucleotide by placement of the biotin moiety as the first or last subunit during synthesis. The sequence is designed with flanking thymidines to provide sites for radiolabeling. A control having the sequence TNNNXNNNT is also prepared in accordance with Examples 3 and 6.

EXAMPLE 10

Preparation of Oligonucleotide Group Comprising Nucleotide Analogs

Oligonucleotide groups having the sequence NNNX-NNNU are prepared in accordance with Example 1 and 6 incorporating one or more of the nucleoside analogs 2'-O-nonyl adenosine, N6-imidazoylpropyl guanosine, 2'-O-aminopentyl cytidine, 2'-O-pentyl-adenosine, 2'-O-pentyl-guanosine, 2'-O-pentyl-cytidine, 3'-terminal 2'-O-methyl uridine and 6-amino-2-hydroxylmethyl-1-hexanol. The nucleosides, 2'-O-nonyl adenosine, N6-imidazoylpropyl guanosine, 2'-O-aminopentyl cytidine, 2'-O-pentyl-adenosine, 2'-O-pentyl-guanosine, 2'-O-pentyl-cytidine, 3'-terminal 2'-O-methyl uridine were prepared by modification of the methods described in PCT US91/00243 filed Jan. 11, 1991. 6-amino-2-hydroxylmethyl-1-hexanol is available commercially. The nucleosides are modified to provide the corresponding phosphoramidite by methods known to those skilled in the art.

EXAMPLE 11

Gel-shift Assay of Random 2-O-Methyl Oligonucleotide Binding to ras RNA Target

The ras 47-mer stem/loop RNA was enzymatically synthesized, $^{32}$P end-labeled according to standard procedures, and gel-purified. 2'-O-Methyl oligonucleotide analog libraries comprising four sets were prepared in accordance with Examples 4 and 6. Each set was tested for binding against the RNA target and a "set $K_D$" was determined in accordance with the following procedure.

In a first round the ras RNA target was incubated at a concentration of approximately 10 pM with each of the four random 2'-O-methyl oligonucleotide sets, at concentrations of 5, 10, 50 and 100 µM in a buffer consisting of 100 mM NaCl and 10 mM MgCl$_2$. The hybridization was carried out for four hours at 37° C., followed by electrophoretic separation of bound vs. unbound material on a 20% acrylamide gel in Tris-Borate buffer (TBE) plus 50 mM NaCl, run at 25 W for four hours. The gel was dried and the radioactive bands were visualized on a phosphorimager (Molecular Dynamics). The ras stem/loop target alone is the lowest band visible on the gel (highest mobility). As this target binds oligonucleotide (non-radioactive), the mobility of the ras target is decreased, shifting the band to a higher position on the gel (complex). In the first gel no binding is seen for the oligonucleotide sets NNNNGNNNN or NNNNUNNNN, but NNNNANNNN shows a slight shift at 100 µM and NNNNCNNNN shifts more than 50% of the target to the bound form at 50 µM oligonucleotide concentration.

The protocol was then repeated in Round 2. The ras RNA target was incubated at a concentration of approximately 10 pM with each of the four random oligonucleotide sets synthesized according to the method described above, at concentrations of 1 and 10 µM to provide the gel image of The second gel shows that oligonucleotide sets NNNNCNANN, NNNNCNGNN and NNNNCNUNN show minimal binding. NNNNCNCNN shows a shift of more than 25% of the target at 1M and about 50% of the target at 10 µM. In Round 3 the ras RNA target was incubated with the random oligonucleotide sets at concentrations of 0.1 and 1 µM to provide the gel image where only NNCNCNCNN showed binding, exhibited by a shift of greater than 50% of the target.

Table 3 sets forth results of nine rounds performed to determine the "winner" sequence which binds to the ras RNA target. $K_D$ are in µM.

TABLE 3

| Round | Sequence* | Q** | $K_D$ A | C | G | U |
|---|---|---|---|---|---|---|
| 1 | NNNNXNNNN | 65,536 | 22 | 10 | >100 | >100 |
| 2 | NNNNCNXNN | 16,384 | >10 | 4 | >10 | >10 |
| 3 | NNXNCNCNN | 4,096 | >10 | 0.5 | >10 | >10 |

TABLE 3-continued

| Round | Sequence* | Q** | $K_D$ | | | |
|---|---|---|---|---|---|---|
| | | | A | C | G | U |
| 4 | NNCXCNCNN | 1,024 | >10 | 0.15 | >10 | >10 |
| 5 | NNCCCXCNN | 256 | 0.08 | >1 | 0.4 | >1 |
| 6 | NNCCCACXN | 64 | 0.05 | >0.5 | 0.08 | >0.5 |
| 7 | NXCCCACAN | 16 | >0.1 | >0.1 | 0.03 | >0.1 |
| 8 | NGCCCACAX | 4 | 0.05 | 0.02 | 0.05 | 0.042 |
| 9 | XGCCCACAC | 1 | 0.03 | 0.05 | 0.02 | 0.01 |

*wherein N is any of A, C, G or T;
**Q is set complexity.

As illustrated in Table 3, it was not difficult to distinguish the set with the lowest $K_D$ (μM) at each round of synthesis and screening.

As expected for oligonucleotide hybridization reactions, positions near the center of the oligonucleotide had a greater effect on the $K_D$ than positions on the extreme 5' or 3' ends. For example, an attempt to fix the 3' position in round 4 did not yield results that distinguished the sets. An alternative position was selected for round 4 which yielded a clear winner, and then the sequence was elucidated from the center of the oligonucleotide to the ends. The final oligonucleotide selected by the procedure is complementary to the single stranded loop region of the target RNA.

EXAMPLE 12

ELISA for Detection of Inhibition of Herpes Simplex Virus-1

ELISA for detection of HSV-1 envelope glycoprotein B (gB) was performed by infection of normal dermal fibroblast cells (NHDF, Clonetics) with HSV-1 (KOS) at a multiplicity of infection of 0.05 PFU/cell. Following virus adsorption, cells were washed and treated with growth media containing oligonucleotide. Oligonucleotides were tested in triplicate wells at four concentrations. Cells were fixed 48 hours postinfection and assayed for the presence of HSV-1 gB antigen by ELISA. Standard deviation were typically within 10%.

EXAMPLE 13

Inhibition of Herpes Simplex Virus-1 Activity by Phosphorothioate Oligonucleotide Sets A group of 65,536 unique 8-mers in 4 sets of 16,348 was prepared in accordance with Examples 3 and 6 each was screened for activity against human herpes simplex virus type 1 (HSV-1) in cell culture in accordance with the procedure described in Example 9. As illustrated in Table 4, antiviral activity was observed with increasing potency at each round of synthesis and screening, with no difficulty discerning the most active set (in bold) in each round.

TABLE 4

| Round | Sequence* | Q** | $IC_{50}$ (μM) when X = | | | |
|---|---|---|---|---|---|---|
| | | | A | C | G | T |
| 1 | NNNXNNNN | 16,348 | >100 | >100 | 70 | >100 |
| 2 | NNNGNNNX | 4,096 | >100 | >100 | 30 | >100 |
| 3 | NNNGNXNG | 1,024 | >100 | >100 | 15 | >100 |
| 4 | NXNGNGNG | 256 | 30 | 30 | 5 | 20 |
| 5 | XGNGNGNG | 64 | 20 | 20 | 1.5 | 20 |

TABLE 4-continued

| Round | Sequence* | Q** | $IC_{50}$ (μM) when X = | | | |
|---|---|---|---|---|---|---|
| | | | A | C | G | T |
| 6 | GGNGXGNG | 16 | 10 | 10 | 1.5 | 10 |
| 7 | GGXGGGNG | 4 | 1.3 | 1.3 | 0.5 | 1.3 |
| 8 | GGGGGXG | 1 | 0.7 | 0.7 | 1.1 | 0.4 |

*where N is any of A, C, G or T;
**where Q is set complexity.

The oligonucleotide set containing a fixed guanine had the most activity in every round of HSV screening except the last round, resulting in selection of a guanine at nearly all fixed positions.

EXAMPLE 14

Optimization of G4 Core Containing 8-mer Oligonucleotide for HSV-1 Antiviral Activity To determine the optimal 8-mer containing a $G_4$ core, a oligonucleotide group was designed as shown in Table 5, using the oligonucleotide cassette GGGG.

TABLE 5

| Sequence* | Most Active X = | $IC_{50}$(μM) |
|---|---|---|
| NNGGGGNX | A | 2.5 |
| NNGGGGXA | T | 1.1 |
| XNGGGGTA | G | 0.8 |
| GXGGGGTA | C | 0.8 |

*N is any of A, G, T or C.

As shown in Table 5, optimization of the sequences surrounding the $G_4$ core produced a 3 fold increase in antiviral activity in four rounds of synthesis and screening, suggesting that although the $G_4$ core is the most important component of the activity, potency can be modulated by the flanking sequences.

EXAMPLE 15

Assay for Detection of Inhibition of Human Immunodeficiency Virus

The human T-lymphoblastoid CEM cell line was maintained in an exponential growth phase in RPMI 1640 with 10% fetal calf serum, glutamine, and antibiotics. On the day of the assay, the cells were washed and counted by trypan blue exclusion. These cells (CEM-IIIB) were seeded in each well of a 96-well microtiter plate at $5 \times 10^3$ cells per well. Following the addition of cells to each well, the compounds were added at the indicated concentrations and serial half log dilutions. Infectious HIV-$1_{IIIB}$ was immediately added to each well at a multiplicity of infection determined to give complete cell killing at 6 days post-infection. Following 6 days of incubation at 37° C., an aliquot of supernatant was removed from each well prior to the addition of the tetrazolium dye XTT to each well. The XTT was metabolized to a formazan blue product by viable cells which was quantitatively measure spectrophotometrically with a Molecular Devices Vmax Plate Reader. The XTT assay measures protection from the HIV-induced cell killing as a result of the addition of test compounds. The supernatant aliquot was utilized to confirm the activities determined in the XTT assay. Reverse transcriptase assays and p24 ELISA were performed to measure the amount of HIV released from the infected cells. Protection from killing results in an increased optical density in the XTT assay and reduced levels of viral reverse transcriptase and p24 core protein.

EXAMPLE 16

Inhibition of Human Immunodeficiency Virus by Phosphorothioate Oligonucleotide Sets A group of 65,536 unique 8-mers in 4 sets of 16,348 each were prepared in accordance with Examples 3 and 6 and screened for activity in accordance with Example 12. The compound sets are described in Table 6. Table 6 sets forth the $IC_{50}$ (µM) for four oligonucleotide sets.

TABLE 6

| Set | Sequence* | $IC_{50}$ (µM) |
|---|---|---|
| A | NNNN A NNN | inactive |
| B | NNNN C NNN | inactive |
| C | NNNN G NNN | 5 |
| D | NNNN T NNN | inactive |

*where N is any of A, C, G, or T.

Set C sowed 50% inhibition of HIV-induced cytopathic effects at 5 µM, while the other compound sets were inactive at concentration up to 25 µM.

EXAMPLE 17

Assay for the Detection of Inhibition of Cytomegalovirus

Confluent monolayer cultures of human dermal fibroblasts were treated with oligonucleotide sets at the indicated concentrations in serum-free fibroblast growth media. After overnight incubation at 37° C., culture medium containing oligonucleotide was removed, cells were rinsed and human cytomegalovirus was added at a multiplicity of infection of 0.1 pfu/cell. After a 2 hour adsorption at 37° C., virus was removed and fresh fibroblast growth medium containing oligonucleotide sets at the indicated concentrations was added. Two days after infection, old culture medium was removed and replaced with fresh fibroblast growth medium containing oligonucleotide sets at the indicated concentrations. Six days after infection media was removed, and cells fixed by addition of 95% ethanol. HCMV antigen expression was quantitated using an enzyme linked immunoassay. Primary reactive antibody in the assay was a monoclonal antibody specific for a late HCMV viral protein. Detection was achieved using biotinylated goat anti-mouse IgG as secondary antibody followed by reaction with streptavidin conjugated B-galactosidase. Color was developed by addition of chlorophenol red B-D-galactopyranoside and absorbance at 575 nanometers measured using an ELISA plate reader. Results are expressed as percent of untreated control and were calculated as follows:

$$\% \text{ Control} = 100 \times \frac{\text{infected cell control} - \text{treated cells}}{\text{infected cell control} - \text{unifected cell control}}$$

EXAMPLE 18

Inhibition of Cytomegalovirus by Phosphorothioate Oligonucleotide Sets

A group of 65,536 unique phosphorothioate 8-mers in 4 sets of 16,438 were prepared in accordance with Examples 3 and 6 and screened for activity against the human cytomegalovirus in accordance with Example 14. The compound sets A (NNNNANNN), B (NNNNGNNN), C (NNNNCNNN) and D (NNNNTNNN), where N is any of A, G, C or T, were screened at a range of concentration from 10 to 200 µM. The results show that compound set B had the greatest activity against cytomegalovirus, causing approximately 20% inhibition at a 100 µM dose and 90% inhibition at a 200 µM dose. Sets A, B and D exhibited minimal to no antiviral activity.

EXAMPLE 19

Assay to Detect Inhibition of Influenza A Virus

Vero cells were pretreated overnight with randomer sets by direct addition to the media at 10 µM and 100 µM concentrations. After overnight treatment cells were infected with influenza A/PR/8 at a MOI of 0.05. Following infection cells were incubated for 48 hours in the presence of oligonucleotide. After incubation cells were fixed with methanol and air dried. Monolayers were then assayed by ELISA for matrix protein. Primary antibody was a monoclonal antibody specific for matrix protein of influenza A virus (B020 Bioproducts for Science). Second antibody was goat anti-mouse IgG conjugated to alkaline phosphatase (BRL, Bethesda, Md.). Substrate was ATTO-PHOS reagent, JBL. Fluorescence was measured using a Millipore Cytofluour 2300 with excitation at 450 nM and emission read at 580 nM.

EXAMPLE 20

Inhibition of Influenza Virus by Phosphorothioate Oligonucleotide Sets

A group of 65,536 unique phosphorothioate 8-mers in 4 sets of 16,438 was prepared in accordance with Examples 3 and 6 and was screened for activity against the Influenza A virus as described in Example 16. The compound sets A (NNNNANNN), B (NNNNGNNN), C (NNNNCNNN) and D (NNNNTNNN), where N is any of A, G, C or T, were screened at 10 µM and 100 µM. The results show that sets C and D had the greatest antiviral activities, set C exhibited approximately 50% inhibition and set D exhibited approximately 35% inhibition of viral activity. A and B exhibited minimal activity.

Data are the arithmetic mean and standard error of triplicate data points of a single experiment.

EXAMPLE 21

Determination of Oligonucleotides which Induce Interferon

A phosphorothioate oligonucleotide group comprising 20 sets having the sequence N N N N X N N N where N is any of adenine, guanine, cytosine or thymidine and X is one of adenine, guanine, cytosine or thymidine is prepared in accordance with Examples 3 and 6. The sets are set forth in Table 7.

TABLE 7

| Set | Modification |
|---|---|
| 1-4 | natural |
| 5-8 | 2'-O-methyl |

TABLE 7-continued

| Set | Modification |
| --- | --- |
| 9-12 | 2'-O-propyl |
| 13-16 | 2'-O-pentyl |
| 17-20 | 2'-O-nonyl |

An ELISA is performed to determine the set which is most effective to induce interferon. The nucleotide in the most effective set is fixed and sets having the fifth position fixed and the fourth position one of adenine, guanine, cytosine or thymidine is prepared. An ELISA is performed to determine the set which is most effective to induce interferon. The steps are repeated until all of the positions are determined.

EXAMPLE 22

Gel Shift Assay of Random Pyrene Oligonucleotide Sets Binding to HIV TAR Element The HIV TAR element is a structured RNA found on the 5'-end of all HIV transcripts. A gel shift has been used to analyze the binding of four oligonucleotide sets to the HIV TAR element. The target RNA has a three base bulge that is required for binding of the transcriptional activation protein tat. The oligonucleotides set forth in Table 8 were prepared in accordance with Examples 5 and 6, each containing a pyrene analog (indicated by A*).

TABLE 8

| | | SEQ ID NO: |
| --- | --- | --- |
| SET 1 | N N N A* N A N N N N | 3 |
| SET 2 | N N N A* N C N N N N | 4 |
| SET 3 | N N N A* N G N N N N | 2 |
| SET 4 | N N N A* N U N N N N | 5 |

The assay uses a 15 pM concentration of the radioactively labeled target and an 0.1, 1, 10, and 100 µM concentrations of each set. Binding of molecules from the set to the target results in a slower mobility complex. Set 3 binds best to TAR wherein 100 µM of the oligonucleotide set caused a shift of approximately 50% of the target. 100 µm of the oligonucleotide set 2 caused a shift of approximately 25% of the target. Sets 1 and 4 caused minimal shift of the target. The sixth position will be fixed as a G and another position unrandomized in the second round of synthesis and assays.

EXAMPLE 23

Random Oligonucleotide Set Binding to HIV gag-pol Triple Strand

Binding to double stranded DNA or RNA is possible by formation of a three stranded complex with the incoming third strand binding in the major groove of the duplex RNA or DNA. The molecular nature of the interaction between the oligomer and target need not be known in order to practice the technique. Thus, it is possible that novel interactions between oligomers and DNA or RNA will be responsible for binding. One of the limitations in the design of triple strand interactions is the need to have a long stretch of homopurines as a target. The 3' (right) side of the gag-pol stem loop is homopurine except for a pair of cytosines near the bottom of the stem. To determine the best oligonucleotide to bind to the gag-pol stem loop, a group of RNA oligonucleotide sets was designed to bind to the purine-rich strand of the gag-pol stem-loop by Hoogstein base pairing and prepared in accordance with Examples 2 and 6. At the position of the two cytosines the sequence was randomized to provide the sequences set forth in Table 9. Binding to the gag-pol stemloop was measured by gel shift analysis as previously described in Example 8 with the following modifications: the radiolabeled gag-pol RNA was incubated with the oligonucleotide in 100 mM NaCl, 25 mM TRIS acetate pH5, 2 mM Mg $Cl_2$, 1 mM spermidine. The gel was a 15% acrylamide with 50 mM NaCl 2 mM $MgCl_2$ added to the running buffer.

The results in Table 9 show that in round 1 the oligonucleotide set CCCUUCCCNUC (SEQ ID NO: 8) had the greatest affinity for the target with a $K_D$ of 50. In the second round the C was fixed in the eighth position and the ninth position was determined. The oligonucleotide CCCUUC-CCCUC (SEQ ID NO: 12) had the greatest affinity for the target in the ninth round with a $K_D$ of 1. Thus, a triple strand-binding sequence can be optimized.

TABLE 9

| Set | Sequence | $K_D$ (µM) | SEQ ID NO: |
| --- | --- | --- | --- |
| Round 1 | | | |
| $A_1$ | CCCUUCCANUC | >100 | 6 |
| $B_1$ | CCCUUCCGNUC | >100 | 7 |
| $C_1$ | CCCUUCCCNUC | 50 | 8 |
| $D_1$ | CCCUUCCUNUC | 100 | 9 |
| Round 2 | | | |
| $A_2$ | CCCUUCCCAUC | 10 | 10 |
| $B_2$ | CCCUUCCCGUC | 10 | 11 |
| $C_2$ | CCCUUCCCCUC | 1 | 12 |
| $D_2$ | CCCUUCCCUUC | 10 | 13 |

EXAMPLE 24

Random Oligonucleotide Binding to Transcription Factors

A radiolabeled oligonucleotide group was prepared having the sequence NNGGGGNX wherein N is any of A, G, T or C and X is one or A, G, T or C as described in Examples 3, 6 and 7. The group was screened for binding to the HIV tat protein, which is a transcription factor produced by the virus as described in Example 24. Binding activity was observed.

EXAMPLE 25

Random 2'-O-Methyl Oligonucleotide Binding to Endothelin-1

Receptor and radiolabeled ligand were supplied in a kit obtained from DuPont/NEN. Assays were performed according to the manufacturer's instructions. A random 2'-O-methyl group was prepared in accordance with Examples 4 and 6 to provide four sets having the sequences GCGNNNANNNNNCGC (SEQ ID NO: 14); GCGNNNGNNNNNCGC (SEQ ID NO:15); GCGNNNCNNNNNCGC (SEQ ID NO:16); GCGNNNUNNNNNCGC (SEQ ID NO: 17) where N is any of A, G, C or U. Each set was diluted to 100 µM in an assay buffer provided in the kit, then incubated with the receptor and ligand as per the manufacturer's protocol. Following the incubation, ligand- bound receptor was separated from unbound by vacuum filtration through glass filters. The bound ligand was then eluted from the filter in scintillation fluid and counted in a scintillation counter. Receptor and ligand were incubated with an excess of unlabeled ligand in order to establish the level of non-specific binding (NSB) to the filters and with no oligonucleotide set (zero) to establish the level of complete binding.

The results shown in Table 10 indicate that set B was most active against Endothelin-1.

TABLE 10

|     | CPM  | NET CPM | % I |
|-----|------|---------|-----|
| NSB | 284  | —       | —   |
| zero| 1421 | 1140    | 100 |
| A   | 1223 | 939     | 82  |
| B   | 1200 | 916     | 80  |
| C   | 1347 | 1063    | 93  |
| D   | 1330 | 1046    | 92  |

EXAMPLE 26

Random 2'-O-Methyl Oligonucleotide Binding to Leukotriene B4

Receptor and radiolabeled ligand were supplied in a kit obtained from DuPont/NEN. Assays were performed according to the manufacturer's instructions. A random 2'-O-methyl group was prepared in accordance with Examples 4 and 6 to provide four sets having the sequences GCGNNNANNNNNNCGC (SEQ ID NO: 14); GCGNNNGNNNNNNCGC (SEQ ID NO:15); GCGNNNCNNNNNNCGC (SEQ ID NO:16); GCGNNNUNNNNNNCGC (SEQ ID NO: 17) where N is any of A, G, C or U. Each set was diluted to 100 µM in an assay buffer provided in the kit, then incubated with the receptor and ligand as per the manufacturer's protocol. Following the incubation, ligand-bound receptor was separated from unbound by vacuum filtration through glass filters. The bound ligand was then eluted from the filter in scintillation fluid and counted in a scintillation counter. Receptor and ligand were incubated with an excess of unlabeled ligand in order to establish the level of non-specific binding (NSB) to the filters and with no oligonucleotide set (zero) to establish the level of complete binding. The results shown in Table 11 indicate that set D was most active against leukotriene B4.

TABLE 11

|     | CPM  | NET CPM | % I |
|-----|------|---------|-----|
| NSB | 383  | —       | —   |
| zero| 1063 | 680     | 100 |
| A   | 989  | 606     | 89  |
| B   | 953  | 570     | 84  |
| C   | 900  | 517     | 76  |
| D   | 894  | 511     | 75  |

EXAMPLE 27

Phosphorothioate and 2'-O-Methyl Oligonucleotide Binding to the Viral Receptors CD4

Two groups of oligonucleotides were prepared. A phosphorothioate oligonucleotide group was prepared in accordance with Examples 3 and 6. A 2'-O-methyl oligonucleotide group was prepared in accordance with Examples 4 and 6. Both groups have the sequence NNNNTNNNN where N is any of A, C, G or T.

100 pmoles of each group of random oligonucleotides is 5' end labeled to high specific activity with $[\gamma-^{32}P]$ ATP and T4 polynucleotide kinase. Each labeled group is reacted with the protein CD4 at room temperature in a buffer consisting of 100 mM KCl, 1.5 mM mgCl$_2$, 0.2 mM EDTA, 10% glycerol, 1 mM DTT, and 20 mM HEPES (pH=7.9). poly dI•dC is added as indicated as a non-specific competitor. After 1 hour protein bound oligonucleotide is separated from unbound by electrophoresis on a 6% native acrylamide gel in 1× TBE buffer. The results of the phosphorothioate oligonucleotide assay indicate binding of the oligonucleotide to the protein. No binding has was detected by the 2'-O-methyl set. Binding has been observed with the phosphorothioate pool against the tat protein.

EXAMPLE 28

Preparation of Random Group of Polypeptides and Assay for Binding Thereof

Polypeptides may be used in the practice of this invention. Monomer amino acids are easily oligomerized into peptides using the appropriate precursor chemicals and instruments available to those skilled in the art, such as those that can be purchased from Applied Biosystems.

The first round of synthesis is as follows:

TABLE 12

| Position | 1 | 2 | 3 | 4 | 5 | 6 | 7 | 8 | 9 |
|----------|---|---|---|---|---|---|---|---|---|
| Set 1    | X | X | X | X | B | X | X | X | X |
| Set 2    | X | X | X | X | A | X | X | X | X |
| Set 3    | X | X | X | X | W | X | X | X | X |
| Set 4    | X | X | X | X | L | X | X | X | X | where A is defined as an acidic amino acid, B is defined as a basic amino acid, W is defined as a neutral amino acid, L is defined as a lipophilic amino acid, and X is defined as any amino acid from the above identified group.

Each of the above sets is tested for inhibition of cell adhesion using a cell culture assay in which the ICAM-1 mediated binding of cells is measured as described. Dustin, M. L. and Springer, T. A. *J. Cell Biol.* 1988, 107, 321. The set showing greatest inhibition of cell adhesion at the lowest polypeptide concentration is selected.

The protocol is repeated, retaining the selected amino acid at position 5, and sequentially testing each remaining position to reach an optimal binding sequence.

EXAMPLE 29

Identification of Oligonucleotide Sequence Using Streptavidin Capture of Biotinylated Target 0.2 µM of a target oligonucleotide having the sequence 3'dBAB AGA CGT CTT GCG 5' (SEQ ID NO: 18) wherein B is biotin, was incubated for 30 minutes at room temperature with 10 µM of a radiolabeled 2'-O-methyl oligonucleotide group prepared in accordance with Examples 4, 6 and 7 having the sequence NNN NCN CNN wherein N is any of adenine, cytosine, thymidine or guanine, and 0.1 µM of a radioactively labeled oligonucleotide complementary to the target (dTCTGCAGAACGC; SEQ ID NO: 19). The target oligonucleotide and any bound radioactively labeled oligonucleotide was captured on streptavidin-coated magnasphere beads (Promega), the beads were washed, and supernatant removed. The captured radioactively labeled oligonucleotide was removed from the beads and run on a polyacrylamide gel. A sample gel indicates that a "winner" can be separated from an excess of random sequence oligonucleotides. The procedure was repeated. In lane 1 was run a 1:10 dilution of the original solution prior to capture. Lane 2 is the supernatant diluted 1:10. Lane 3 is the bound material from the first round. A band of "winner" sequence is apparent, migrating to the first arrow. Lanes 4 and 5 are the supernatant (1:10 dilution) and bound material from the second round, respectively. The second round results in a "winner" band of greater purity. Lanes 6 and 7 are the supernatant (1:10 dilution) and bound material from the third round, respectively. The supernatant does not contain any radiolabeled oligonucleotides. The third round results in a "winner" band with little to no non-specific oligonucleotide.

EXAMPLE 30

Identification of a Protein Target

A group of oligonucleotides having the sequence NNNNNNNN wherein N is any one of adenine, guanine, thymidine or cytosine is prepared in accordance with Examples 3 and 6. The group is labeled using [γ-$^{32}$P] ATP and T4 polynucleotide kinase.

In individual wells of a 96-well nitrocellulose filter manifold, the following proteins are incubated in a solution of phosphate buffer saline: plasminogen activator $A_2$, tumor necrosis factor a, tumor necrosis factor β and gp120. Phosphate buffer saline only is added to a control well. The filter is washed. An aliquot of the labeled group of oligonucleotides is added to each well and incubated at room temperature for 10 minutes. The filter is washed and the counts in each well over background are counted to determine whether binding of the oligonucleotide to the protein occurred.

EXAMPLE 31

Determination of Phosphorothioate Oligonucleotide Having Binding Affinity for Nitrocellulose Bound Proteins An oligonucleotide analog group comprising four sets of oligonucleotides eight positions in length is prepared in accordance with Examples 3 and 6 and each set is tested for binding against the nitrocellulose-bound proteins identified in accordance with Example 27. The set having the highest affinity for each protein, as indicated by counts per well is the "winner set" for each protein. Results of the first round are as set forth in Table 13.

TABLE 13

| Position | 1 | 2 | 3 | 4 | 5 | 6 | 7 | 8 | Protein winner |
|---|---|---|---|---|---|---|---|---|---|
| Set 1 | N | N | N | N | A | N | N | N | plasminogen activator $A_2$, tumor necrosis factor α |
| Set 2 | N | N | N | N | G | N | N | N | no winner |
| Set 3 | N | N | N | N | C | N | N | N | gp120 |
| Set 4 | N | N | N | N | T | N | N | N | tumor necrosis factor β |

The filter is washed and wells counted. In a second round, the A is fixed in the fifth position and the sets (NNNAANNN), (NNNGANNN), (NNNCANNN), and (NNNTANNN) are prepared for testing in the wells containing plasminogen activator $A_2$ and tumor necrosis factor α. Similarly, sets in which the C is fixed in the 5th position or a T is fixed in the 5th position are prepared for testing in the gp120 and tumor necrosis factor β wells, respectively. By the eight round, "winner" sequences for all four target proteins are determined.

EXAMPLE 32

Determination of an Oligonucleotide Having Binding Affinity for a Target Protein using Subfractionated Sets of Oligonucleotides An oligonucleotide analog group comprising four sets of oligonucleotides eight positions in length is prepared in accordance with Examples 3 and 6 wherein each of the sets has a different one of adenine, guanine, thymidine and cytosine in the 5th position, and the rest of the positions are randomized to provide the group: NNNNANNN, NNNNGNNN, NNNNTNNN, and NNNNCNNN. Each set is subfractionated by charge with an anion exchange column. Each subfraction is tested for affinity for the target protein by gel shift assay. The subfraction from the set having an adenine in the 5th position has the highest binding affinity. In a further round, the 5th position is fixed to contain an adenine in the 5th position, and each set has a different nucleotide in the fourth position to provide the group NNNAANNN, NNNTANNN, NNNGANNN, and NNNCANNN. The sets are again subfractionated by charge with an anion exchange column and the subfractions are tested for affinity for the target protein by gel shift assay. The steps are repeated until each position is determined.

EXAMPLE 33

Determination of an Oligonucleotide Having Binding Affinity for the NF-kB Site Binding Transcription Factor c-rel Using a Capture Assay c-rel has been shown to represent a constituent of the NF-kB site binding transcription factor, which plays a crucial role in the expression of a number of genes including the immunoglobulin k light chain gene, IL-2ra, and MHC. Gilmore, et al., *Cell* 1986, 62, 791.

Crude nuclear extracts were prepared as detailed by Franza, et al., *Nature* 1987, 330, 391, from Jurkat cells stimulated 4 hours with 1 μM PHA and 100 nM PMA to induce the expression of rel. The extract was then preabsorbed with 100 μl streptavidin agarose per ml for 10 minutes. This was followed with the addition of poly dI.dC as a non specific competitor at a concentration of 100 μg/ml of extract.

Phosphorothioate oligonucleotides were synthesized with the sequence GGG GAC TTT CCG CTG GGA CTT TCT AG-B (SEQ ID NO: 22) and CTG GAA AGT CCC AGC GGA AGG TCC CC-B (SEQ ID NO:23), where B=biotin, as described in Examples 3 and 9. The complementary oligonucleotides were then hybridized to create the double stranded NF-kB binding site, which was used as a positive control in the assay. A combinatorial phosphorothioate library was also synthesized with the general sequence TNNNXNNNT-B, where X=A, G, C, or U as described in Examples 3 and 6.

Each pool of the library was incubated in triplicate at a concentration of 1 μM with 100 μl of the extract for 20 minutes at room temperature. As a positive control, the native double stranded NF-kB binding site was incubated at 100 nM with the same amount of extract. Following the incubation each mixture was added to streptavidin coated microtiter plates (Elkay Lab Systems) and incubated 20 minutes. Unbound molecules were washed away with PBS.

10 μl of PBS plus 5% fetal calf serum was added to each well for 20 minutes at room temperature followed by aspiration and addition of 100 μl of 1:500 tat antisera in PBS plus 1% FCS for 2 hours at room temperature. The wells were then washed with PBS and 100 μl of 1:5000 Protein A/G-alkaline phosphatase (Pierce) added in PBS for 2 hours at room temperature. Excess Protein A/G-Alkaline phosphatase was removed by washing with PBS then 200 μl PNPP substrate added. Color development was measured 2 hours later by reading absorbance at 405 nM on a Titertek Multiscan ELISA plate reader.

The results are shown in FIG. 1. As expected the native NF-kB binding site binds the greatest amount of rel (+lane). A rel binding site with a 2 base pair mutation bound less than 5% of that bound by the +control (data not shown). The pools of the P=S library bind differential amounts of rel with the A pool binding the least and the C pool binding the greatest amount.

EXAMPLE 34

Determination of an Oligonucleotide Having Binding Affinity for the HIV-tat Protein Using a Competition Assay All HIV mRNAs contain a stable hairpin structure known as TAR on the extreme 5' end of the message. This region has been shown to specifically bind an HIV regulatory protein known as tat. The mechanisms mediating increased gene expression have been intensely studied and may involve increased transcriptional efficiency. Cullen, et al., Cell 1990, 63, 655.

A truncated version (residues 16–45; ΔTAR) of the TAR hairpin previously shown to bind tat was synthesized using 2'-O-methyl oligonucleotides as described in Example 4 and was biotin conjugated on the 3' end (ΔTAR-B) as described in Example 9. A combinatorial library was synthesized using RNA oligonucleotides with the sequence CCA NNX NNN NGC CUG GGA GCN NNN UGG, where X=A (SEQ ID NO:24), G (SEQ ID NO:25), C (SEQ ID NO:26), or U (SEQ ID NO:27) as described in Example 2 and 6.

The pools of the library at 0, 1, 10, or 100 μM were incubated with 100 μl of purified recombinant tat transcription factor (Repligen) at a concentration of 20 pg/μl for 15'. This and all other steps were carried out at room temperature. The competitor, ΔTAR-B, was then added at a concentration of 100 nM. Following a 20' incubation, the mixture was bound to streptavidin-coated microtiter plates as in Example 33. After the non-bound molecules were washed away with PBS, 100 μl of 1:500 tat antisera was added to each well for 2 hours. Protein A/G-alkaline phosphatase was bound to the tat antibodies followed by the addition of the PNPP substrate and quantitation of A 405 as detailed in Example 33.

Figure 2:
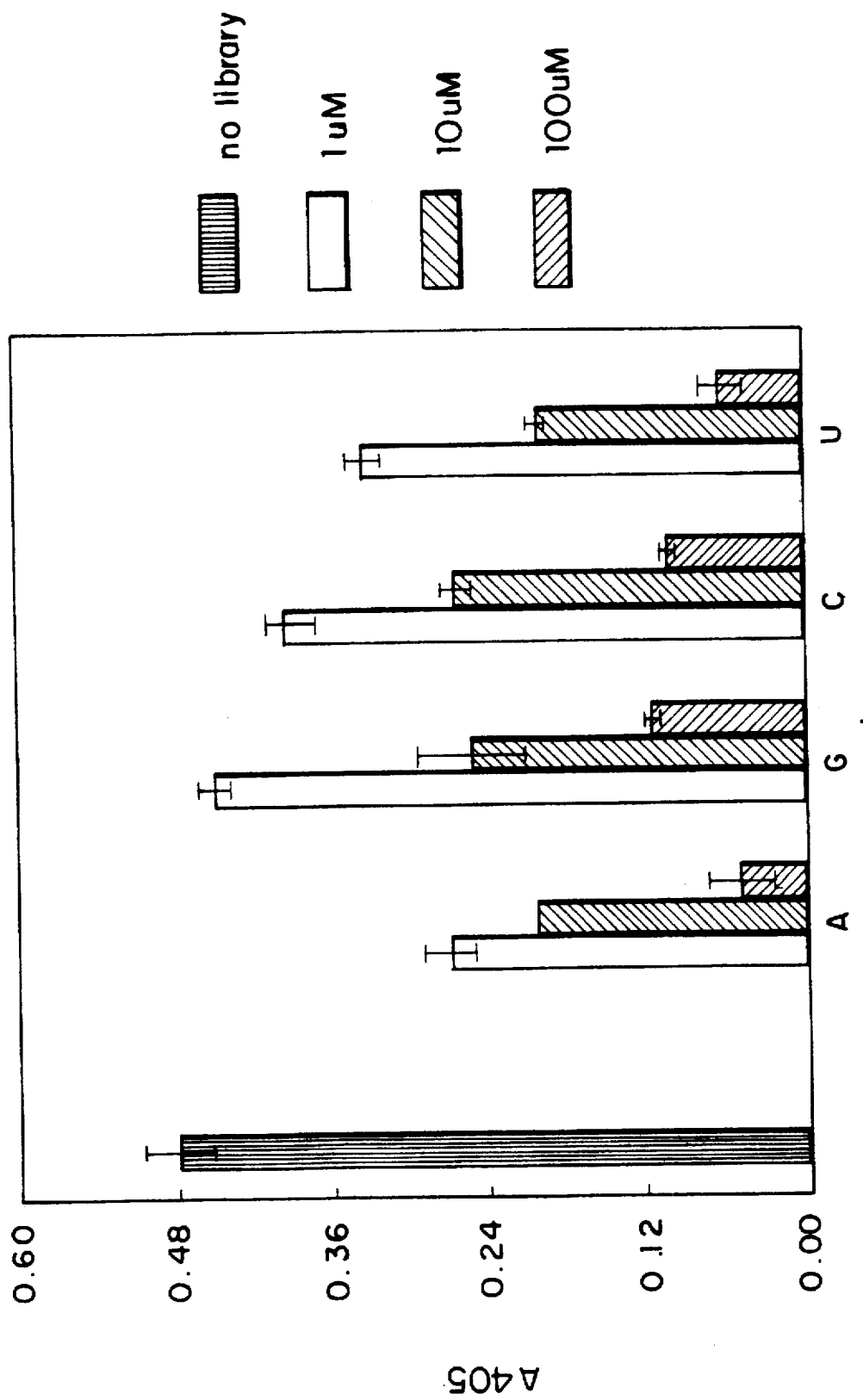
FIG. 2 is a schematic representation showing binding affinity of four sets of RNA oligonucleotides for the HIV-tat element at 1 μM, 10 μM and 100 μM concentrations. The RNA oligonucleotide set having the sequence CCAN-NANNNNGCCUGGGAGCNNNNUGG (SEQ ID NO:24) bound to HIV-tat most specifically at all three concentrations as evidenced by the reduced amount of the TAR element bound by tat.

The results are shown in FIG. 2. In the competition mode library pools which bind the transcription factor prevent binding to the natural target (in this case the competitor ΔTAR) also present in the assay. Since only the natural target is biotinylated, only target proteins which are able to bind it will remain in the plate after washing with PBS. Therefore pools which retain more transcription factor should lower the amount of protein available to bind the natural target and therefore the overall signal. In this example the pool containing A at the fixed position inhibits binding of tat to ΔTAR to the greatest extent, whereas the pool fixed at G has the least effect. If the ΔTAR was bound with a molecule known to disrupt the tat binding site, no signal was observed (data not shown).

EXAMPLE 35

Figure 3:
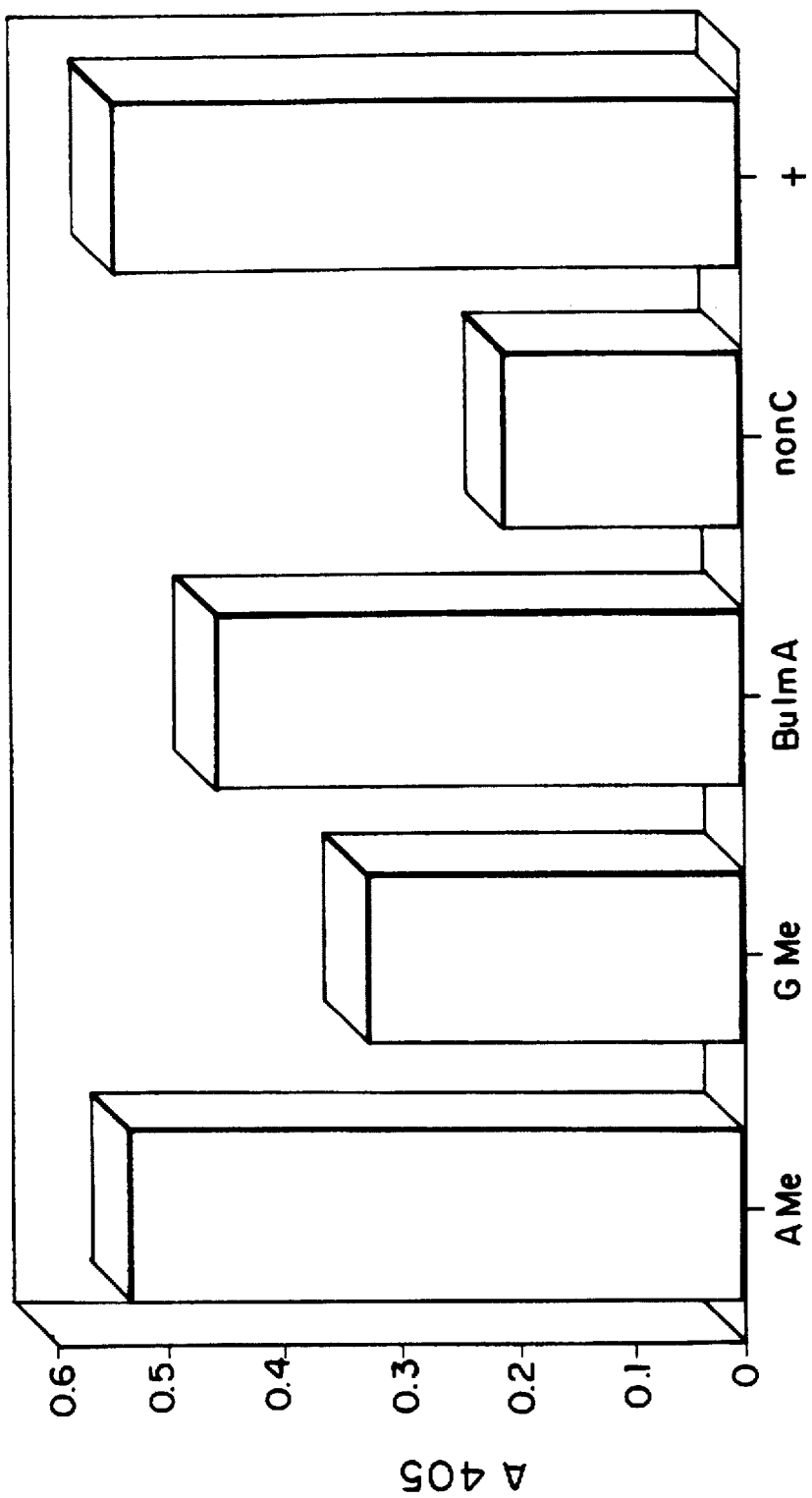
FIG. 3 is a schematic representation showing binding affinity of four sets of oligonucleotides for the HIV-tat protein using a competition assay. The oligonucleotide having the sequence TNNN(non C)NNNT exhibited the highest binding activity. The oligonucleotide having the sequence TNNN(A Me)NNNT exhibited the least binding activity.

Determination of an Oligonucleotide Having Binding Affinity for the HIV-tat Protein Using a Competition Assay A combinatorial library having the sequence TNNNXNNNT, where X is A Me, G Me, BiIm A or NonC, was prepared as described in Examples 1 and 6. 100 μM of each pool of oligonucleotides was tested for binding affinity for the HIV-tat protein as described in Example 34. Results are shown in FIG. 3. In this example the pool containing nonC at the fixed position inhibits binding of tat to ΔTAR to the greatest extent, whereas the pool fixed at A Me has the least effect.

EXAMPLE 36

Figure 4:
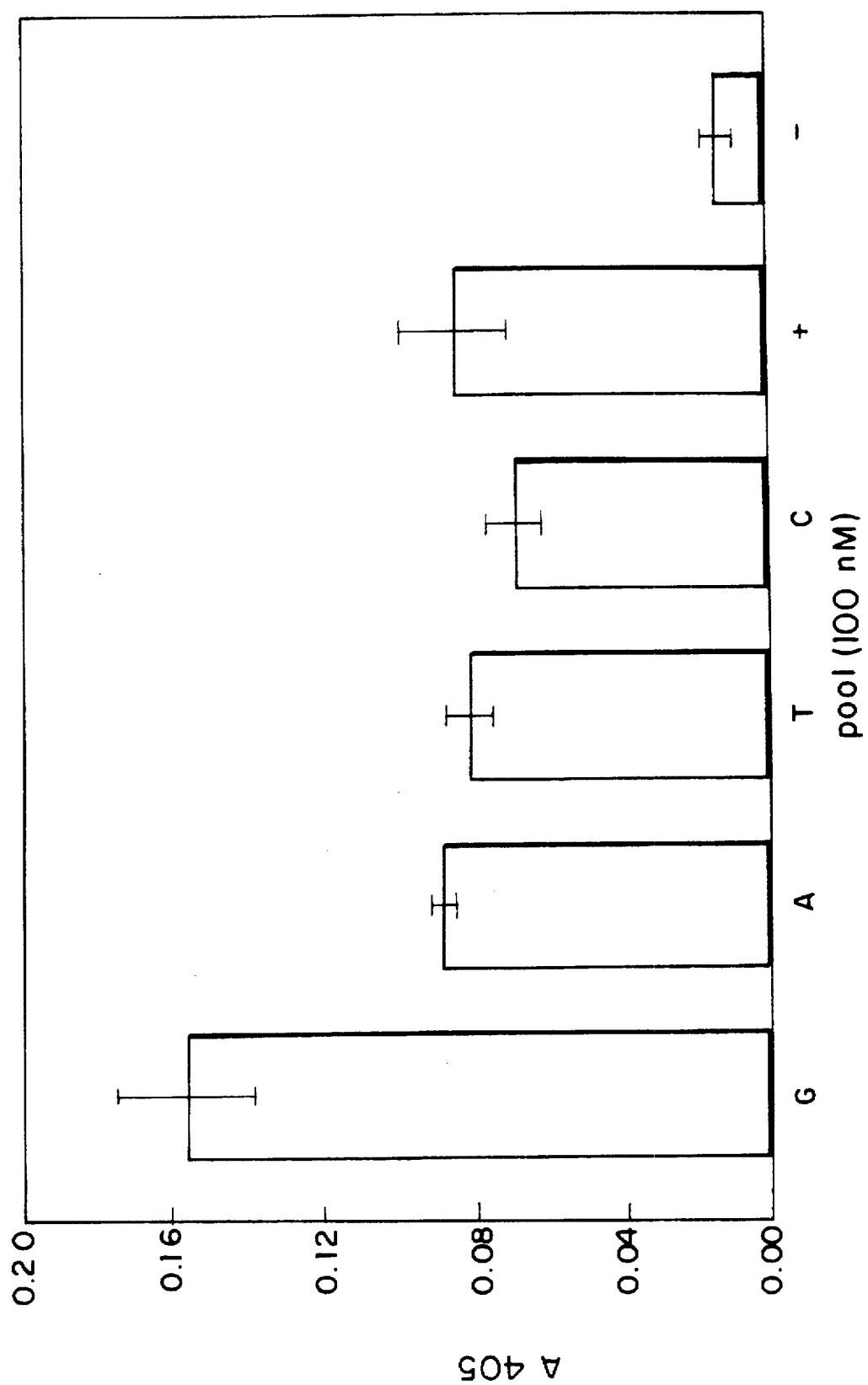
FIG. 4 is a schematic representation showing binding affinity of four sets of oligonucleotides for the HIV-tat protein using a capture assay. The phosphorothiate oligonucleotide having the sequence TNNNGNNNT-B exhibited the highest binding activity. The phosphorothioate oligonucleotide having the sequence TNNNCNNNT-B exhibited the least binding activity.

Determination of an Oligonucleotide Having Binding Affinity for the HIV-tat Protein Using a Capture Assay Each pool of the phosphorothioate combinatorial library described in Example 33 was incubated at a concentration of 100 nM with tat protein as described in Example 34. Following incubation of the protein with the library pools, the complexes were captured on streptavidin plates and binding quantitated as in Example 33. The results are shown in FIG. 4. The P=S library is much less subject to nuclease degradation than the RNA ΔTAR structure, which accounts for the substantial activity of all pools of the library. However, the pool fixed at G clearly binds more tat than the others.

EXAMPLE 37

Determination of an Oligonucleotide Having Binding Affinity for the c-myc Nuclear Protein Using a Competition Assay Myc is nuclear protein which functions in cell proliferation, differentiation and neoplastic disease, Nissen, et al., Cancer Research 1986, 46, 6217. It has been shown to bind DNA in a sequence specific manner. Blackwell, et al., Science 1990, 250, 1149.

Crude nuclear extracts were prepared from HL 60 cell as detailed in Example 33. These cells have been shown to express myc at high levels {3641}. Phosphorothioate oligonucleotides were synthesized with the sequence GAT CCC CCC ACC ACG TGG TGC CTG A-B (SEQ ID NO:28) and GAT CTC AGG CAC CAC GTG GTG GGG G-B (SEQ ID NO:29) as described in Examples 3 and 9. The oligonucleotides were then hybridized to create the double stranded myc binding site to act as a competitor. A combinatorial 2'-O-methyl library was also synthesized with the general sequence GCGNNNXNNNNNNCGC; where X=A (SEQ ID NO:30), G (SEQ ID NO:31), C (SEQ ID NO:32), or U (SEQ ID NO:33) as described in Examples 4 and 6.

Each pool of the library was incubated in triplicate at a concentration of 50 μM with the HL-60 extract described above. The myc P=S binding site was then added to the mixes followed by incubations and washes as detailed in Example 34. An antibody directed to the leucine zipper region of the myc protein (Santa Cruz Biotechnology) was added at a 1:1000 dilution. myc bound to biotinylated c-myc transcription factor was quantitated as described in Example 34.

Figure 5:
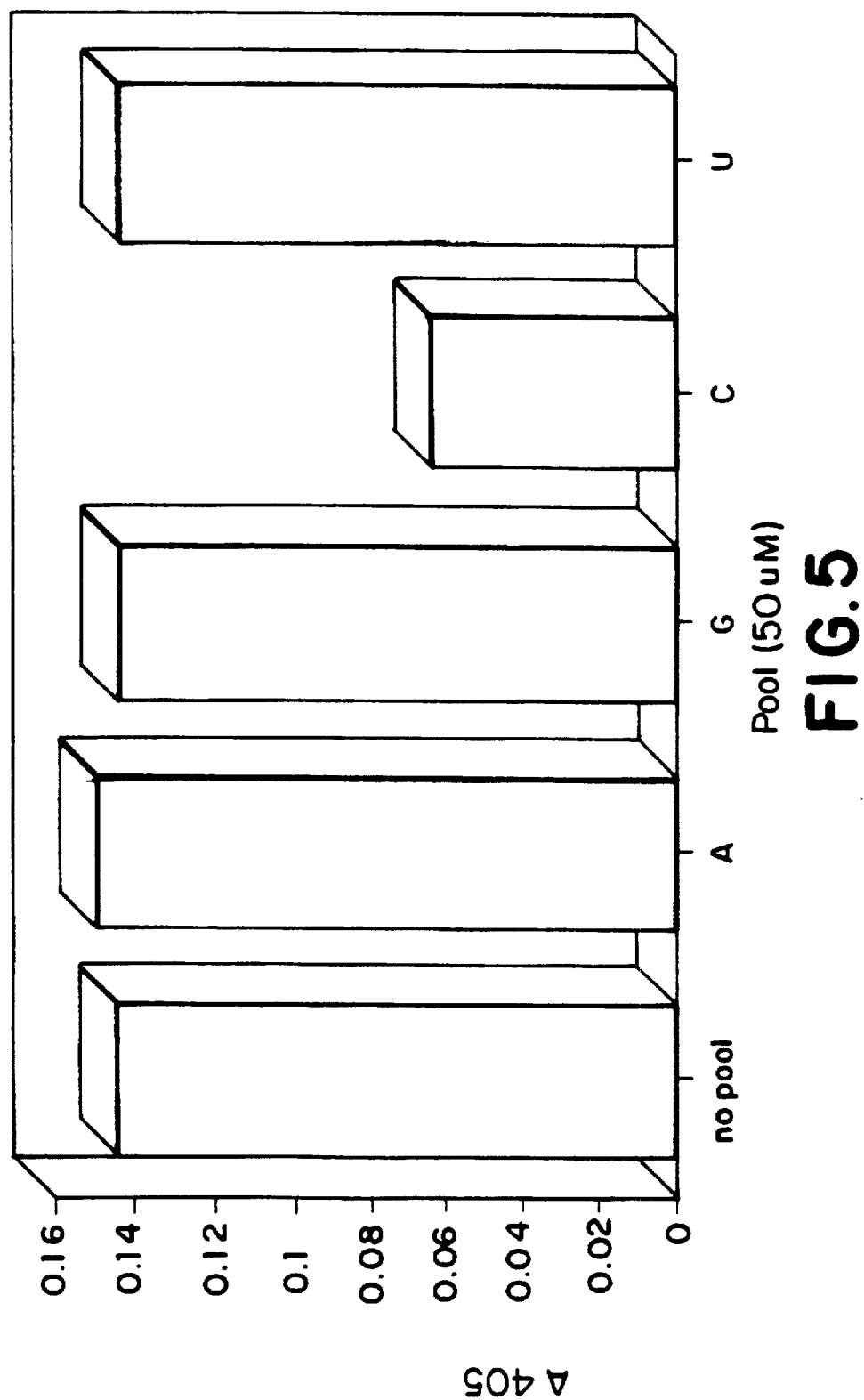
FIG. 5 is a schematic representation showing binding affinity of four sets of 2'-O-methyl oligonucleotides for the c-myc nuclear protein. The 2'-O-methyl oligonucleotide set having the sequence GCGNNNCNNNNNNCGC (SEQ ID NO:33) bound with c-myc most specifically as evidenced by the reduced amount of c-myc binding to a double stranded c-myc binding site.

The results are shown in FIG. 5. In this example the pool with X=C inhibits binding of myc to its natural binding site

31 probe by approximately 50%, while the other pools have little to no effect on myc binding. No appreciable binding of myc was detected to a scrambled version of the binding site (data not shown).

EXAMPLE 38

Figure 6:
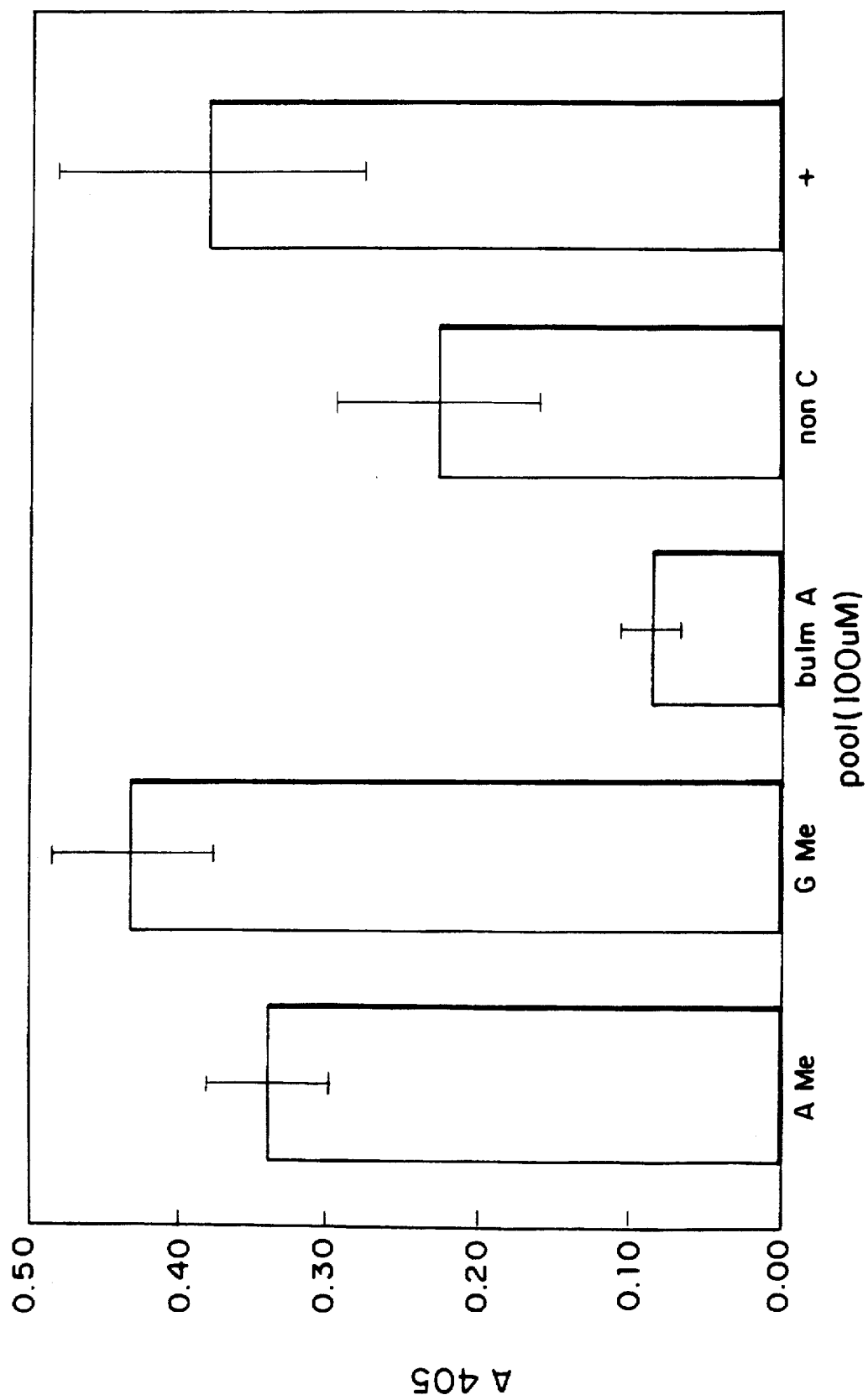
FIG. 6 is a schematic representation showing binding affinity of four sets of oligonucleotides for c-myc protein using a competition assay. The oligonucleotide having the sequence TNNN(biIM A)NNNT exhibited the highest binding activity. The oligonucleotide having the sequence TNNN(G Me)NNNT exhibited the least binding activity.

Determination of an Oligonucleotide Having Binding Affinity for the c-myc Nuclear Protein Using a Competition Assay A combinatorial library having the sequence TNNNXNNNT, where X is A Me, G Me, BiIm A or NonC, was prepared as described in Examples 1 and 6. Each pool of the library was incubated in triplicate at a concentration of 100 μM with the HL-60 lysate in competition with the myc P=S binding site at a concentration of 100 nM. The results, shown in FIG. 6, demonstrate that the pool fixed at BiIm A has the greatest ability to disrupt c-myc association to its natural DNA binding site.

EXAMPLE 39

Determination of an Oligonucleotide Having Binding Affinity for the c-rel Transcription Factor Using a Competition Assay Nuclear extracts containing c-rel transcription factor and the biotinylated NF-kB binding site competitor were prepared as detailed in Example 33. A combinatorial library was synthesized with the general sequence TNNNXNNNT: where X=Me A, Me G, nonyl C, or buIm A as described in Examples 1 and 6.

Each pool of the library was incubated at either 20 or 100 μM with 100 μl of the extract. This was followed by the addition of the NF-kB binding site competitor. Following the wash antibody to rel was added as in Example 33. The amount of rel bound was quantitated as in Example 34.

Figure 7:
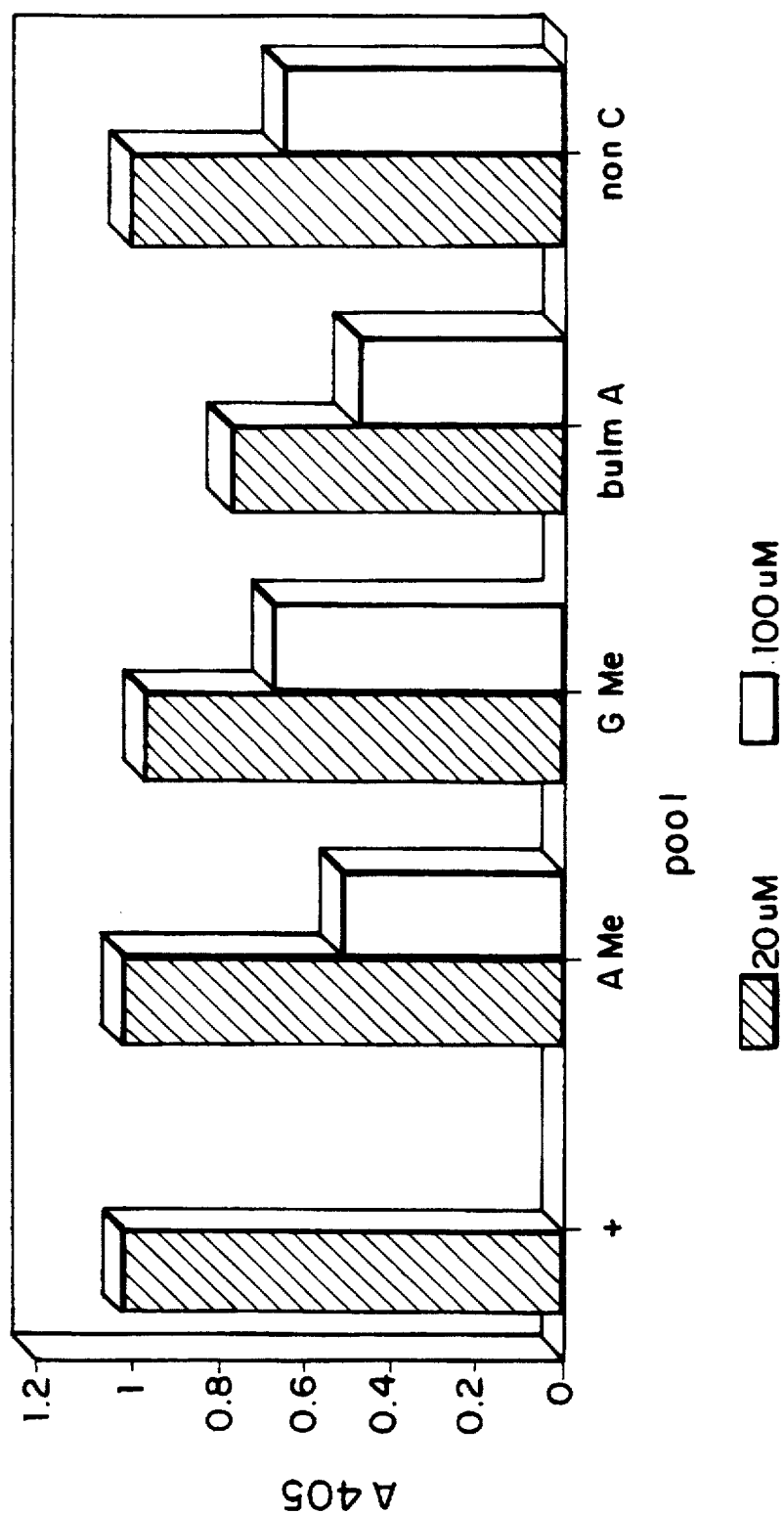
FIG. 7 is a schematic representation showing binding affinity of four sets of oligonucleotides for the c-rel protein. The oligonucleotide having the sequence TNNN(BuImA)NNNT competed most effectively with the NF-kB binding site exhibiting the highest binding activity. The oligonucleotide having the sequence TNNN(nonylC)NNNT exhibited the least binding activity.

The results, shown in FIG. 7, indicate that the pool where X=buIm A, binds the greatest amount of rel. The pool fixed at nonyl C has the least affinity for the rel.

Figure 8:
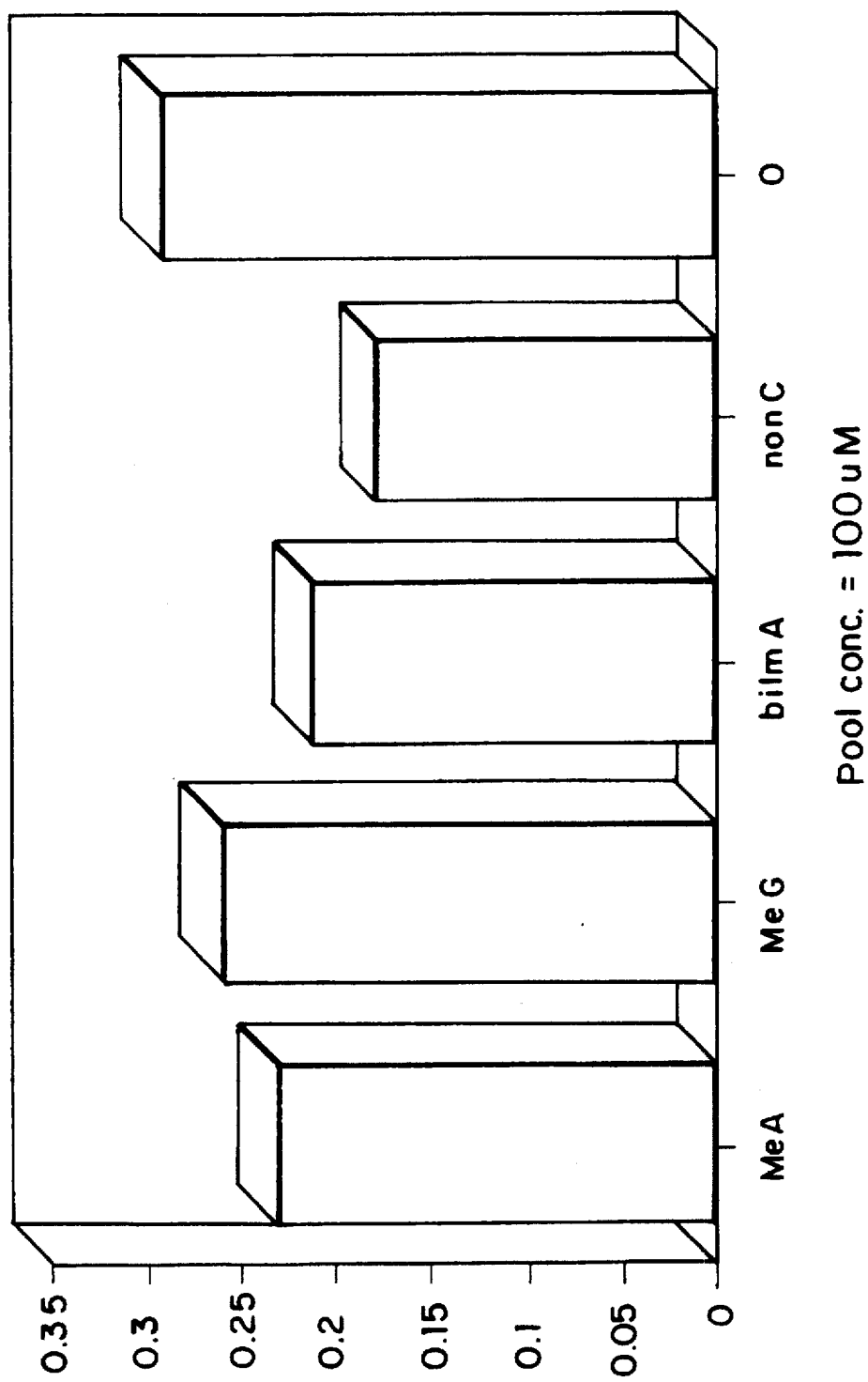
FIG. 8 is a schematic representation showing binding affinity of four sets of oligonucleotides for c-rel using a competition assay. The oligonucleotide having the sequence TNNN(nonyl C)NNNT exhibited the highest activity. The oligonucleotide having the sequence TNNN(G Me)NNNT exhibited the least binding activity.

A second combinatorial library was synthesized based upon the first round winner. The library has the general sequence TNNX(buImA)NNNT: where X=Me A, Me G, nonyl C, or buIm A as described in Examples 1 and 6. The pools of the library were tested for inhibition of rel binding as described above. The results, as shown in FIG. 8, indicate that the pool fixed at nonyl C gave the greatest amount of inhibition.

EXAMPLE 40

Determination of an Oligonucleotide Having Binding Affinity for the AP-1 Transcription Factor Using a Competition Assay Genes belonging to the Fos and Jun oncogene families encode nuclear proteins associated with a number of transcriptional complexes {3643}. c-jun is a major component of the AP-1 binding site which was originally shown to regulate TPA induced expression of responsive genes through the TPA response element (TRE). The June protein forms homo- or heterodimers which bind the TRE, but the Fos protein is only active as a heterodimer with any of the Jun family of proteins. Fos/Jun heterodimers have a much higher affinity for the TRE than Jun homodimers {3644}.

Figure 9:
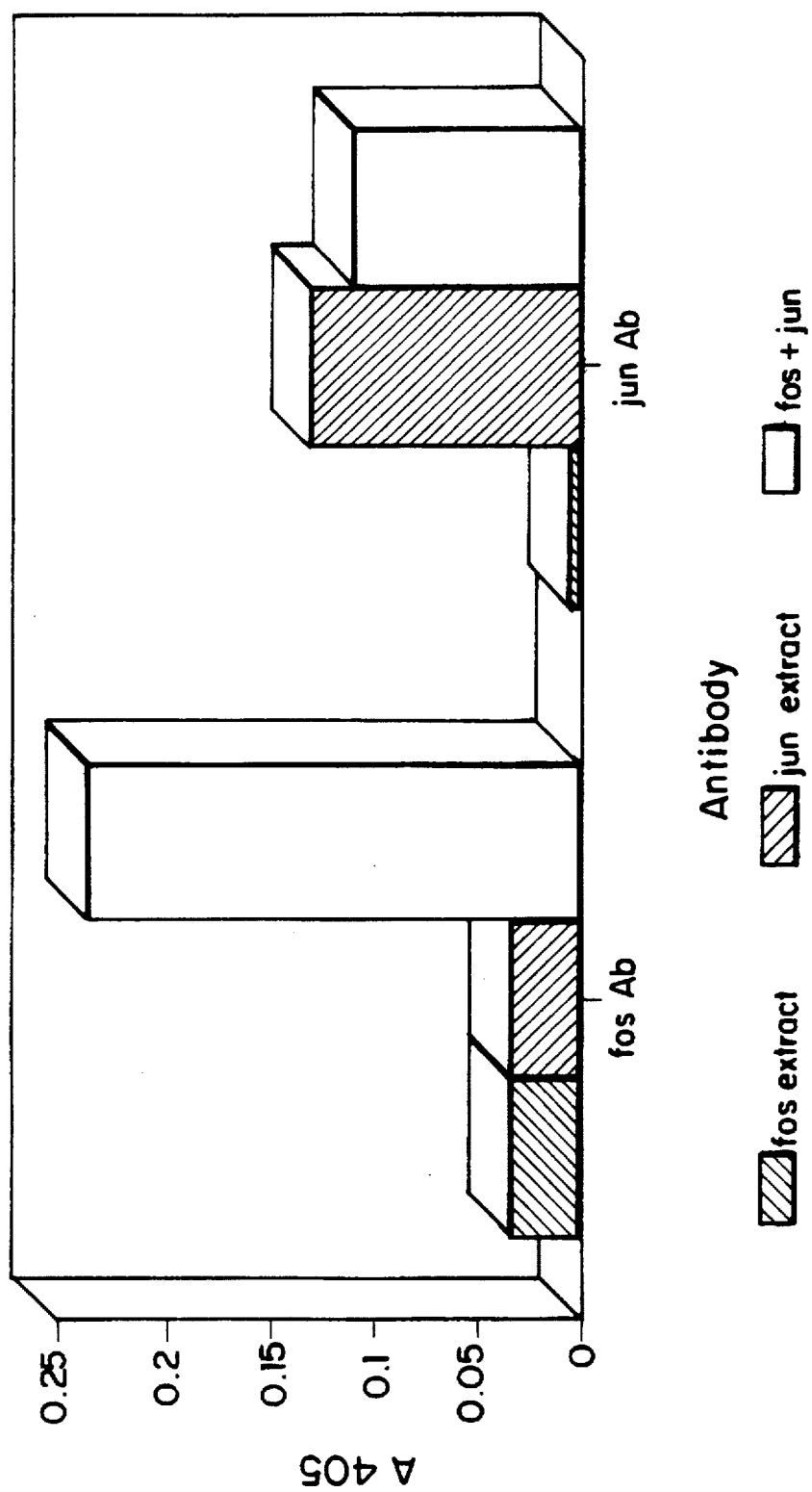
FIG. 9 is a schematic representation showing binding of fos and jun to Ab-1 transcription factor.

Both the fos and the jun cDNA have been cloned downstream of the Sp6 promoter. RNA was produced from each plasmid in vitro, then used to produce functional jun and fos proteins in rabbit reticulocyte lystates. The fos and jun proteins were then allowed to bind to the biotintylated AP-1 binding site. Binding was quantitated with an antibody directed to fos or jun. The results are shown in FIG. 9.

When the fos alone is incubated with the AP-1 site there is no detectable binding with either antibody. When the jun alone is incubated with the binding site, a signal is detected with only the jun antibody. This is consistent with the formation of a jun homodimer, which has previously been demonstrated to bind AP-1. When the fos and jun proteins are mixed a signal is detected with both fos and jun antibodies. This is consistent with the formation of a fos/jun homodimer which is known to bind the AP-1 site and should be detectable with either antibody.

Libraries of the present invention can be tested for the ability to block the formation of the fos/jun heterodimer. Molecules which block formation should decrease the signal detected with the fos antibody, but not the jun antibody.

---

What is claimed is:

1. A method for determining the sequence of an oligonucleotide having specific binding activity for a transcription factor comprising the steps of:

(a) preparing a group comprising a plurality of sets of oligonucleotides, each oligonucleotide comprising at least four nucleotides, by:
  i. defining a common position in the oligonucleotides of the sets,
  ii. synthesizing said sets of oligonucleotides such that each set has a different nucleotide in said common position, the nucleotides which are not in said common position being randomized, and
  iii. modifying the oligonucleotides of the sets of oligonucleotides with linker moieties for attaching the oligonucleotides to a solid support;

(b) incubating each of said sets of oligonucleotides with the transcription factor under binding conditions to form oligonucleotide-transcription factor complexes;

(c) attaching the sets of oligonucleotides to a solid support via the linker moiety;

(d) separating bound from unbound transcription factor;

(e) detecting the binding of transcription factor to each set of oligonucleotides attached to solid support where greatest binding is indicative of highest specific binding activity;

(f) selecting the set having the highest activity;

(g) preparing a further group comprising a plurality of sets of oligonucleotides, each of the sets having in the previous common position the nucleotide appearing in the previously defined common position in the selected one of the previous group of sets; each set of said further group of sets having a different nucleotide in an additional common position, the nucleotides in the position of the oligonucleotide which are not in a common position being randomized;

(h) modifying the oligonucleotides of the sets of oligonucleotides with linker moieties for attaching the oligonucleotides to a solid support;

(i) incubating each of said sets of oligonucleotides with the transcription factor under binding conditions to form oligonucleotide-transcription factor complexes;

(j) attaching the sets of oligonucleotides to a solid support via the linker moiety;

(k) separating bound from unbound transcription factor;

(l) detecting the binding of transcription factor to each set of oligonucleotides attached to solid support where greatest binding is indicative of highest specific binding activity;

(m) selecting the set having the highest activity; and (n) performing steps (g) through (m) iteratively until the sequence of at least one oligonucleotide having specific binding activity for the transcription factor has been determined.

2. The method of claim 1 wherein the step of attaching to the solid support comprises contacting sets of oligonucleotides to a streptavidin-coated solid support, the linker moiety being biotin.

3. The method of claim 1 wherein the step of detecting the binding of transcription factor comprises contacting each set

47 of oligonucleotides with an antibody specific for the transcription factor.

4. The method of claim 1 further comprising a coincubating the sets of oligonucleotides with a competitor under binding conditions.

5. The method of claim 4 wherein the transcription factor is c-myc and the competitor is a double stranded c-myc binding site wherein the first strand of the double stranded binding site is comprised of an oligonucleotide having the sequence (SEQ ID NO:28) and the second strand of the double stranded binding site is comprised of an oligonucleotide having the sequence (SEQ ID NO:29).

6. The method of claim 4 wherein the transcription factor is HIV-tat protein and the competitor is at least a portion of TAR.

7. The method of claim 4 wherein the transcription factor is c-rel and the competitor is the NF-kB binding site.

8. The method of claim 1 wherein the attaching step follows the incubation step.

9. A method for determining the sequence of an oligonucleotide having specific binding activity for a transcription factor comprising the steps of:

(a) preparing a group comprising a plurality of sets of oligonucleotides, each oligonucleotide comprising at least four nucleotides, by:
  i. defining a common position in the oligonucleotides of the sets,
  ii. synthesizing said sets of oligonucleotides such that each set has a different nucleotide in said common position, the nucleotides which are not in said common position being randomized, and
  iii. detectably labeling oligonucleotides of each set of oligonucleotides;

(b) modifying the transcription factor with a linker moiety for attaching the transcription factor to a solid support;

(c) incubating each of said sets of oligonucleotides with the transcription factor under binding conditions to form oligonucleotide-transcription factor complexes;

(d) attaching the transcription factor to a solid support via the linker moiety;

(e) separating bound from unbound oligonucleotide;

(f) detecting the binding of each oligonucleotide set to the transcription factor attached to solid support where greatest binding is indicative of highest specific binding activity;

(g) selecting the set having the highest activity;

(h) preparing a further group comprising a plurality of sets of oligonucleotides, each of the sets having in the previous common position the nucleotide appearing in the previously defined common position in the selected one of the previous group of sets; each set of said further group of sets having a different nucleotide in an additional common position, the nucleotides in the position of the oligonucleotide which are not in a common position being randomized;

(i) detectably labeling oligonucleotides of each set of oligonucleotides;

(j) modifying the transcription factor with a linker moiety for attaching the transcription factor to a solid support;

(k) incubating each of said sets of oligonucleotides with the transcription factor under binding conditions to form oligonucleotide-transcription factor complexes;

(l) attaching the transcription factor to a solid support via the linker moiety;

(m) separating bound from unbound oligonucleotide;

48

(n) detecting the binding of each oligonucleotide set to transcription factor attached to solid support where greatest binding is indicative of highest specific binding activity;

(o) selecting the set having the highest activity; and (p) performing steps (h) through (o) iteratively until the sequence of at least one oligonucleotide having specific binding activity for the transcription factor has been determined.

10. The method of claim 9 wherein the step of attaching to the solid support comprises contacting the transcription factor to a streptavidin-coated solid support, the linker moiety being biotin.

11. The method of claim 9 wherein the step of preparing a group comprising a plurality of sets of oligonucleotides comprises radiolabeling each set of oligonucleotides.

12. The method of claim 9 further comprising coincubating the sets of oligonucleotides with a competitor under binding conditions.

13. The method of claim 12 wherein the transcription factor is c-myc and the competitor is a double stranded c-myc binding site wherein the first strand of the double stranded binding site is comprised of an oligonucleotide having the sequence (SEQ ID NO:28) and the second strand of the double stranded binding site is comprised of an oligonucleotide having the sequence (SEQ ID NO:29).

14. The method of claim 12 wherein the transcription factor is HIV-tat protein and the competitor is at least a portion of TAR.

15. The method of claim 12 wherein the transcription factor is c-rel and the competitor is the NF-kB binding site.

16. The method of claim 9 wherein the attaching step follows the incubation step.

17. A method for determining the sequence of an oligonucleotide having specific binding activity for a transcription factor comprising the steps of:

(a) preparing a group comprising a plurality of sets of oligonucleotides, each oligonucleotide comprising at least four nucleotides, by:
  i. defining a common position in the oligonucleotides of the sets, and
  ii. synthesizing said sets of oligonucleotides such that each set has a different nucleotide in said common position, the nucleotides which are not in said common position being randomized;

(b) modifying the transcription factor with a linker moiety for attaching the transcription factor to a solid support;

(c) incubating each of said sets of oligonucleotides with the transcription factor under binding conditions to form oligonucleotide-transcription factor complexes;

(d) adding a competitor under binding conditions to form transcription factor-competitor complexes;

(e) attaching the transcription factor to a solid support via the linker moiety;

(f) separating bound from unbound competitor;

(g) detecting the binding of the competitor to the transcription factor attached to solid support where lowest binding is indicative of highest oligonucleotide specific binding activity;

(h) selecting the set having the highest activity;

(i) preparing a further group comprising a plurality of sets of oligonucleotides, each of the sets having in the previous common position the nucleotide appearing in the previously defined common position in the selected one of the previous group of sets; each set of said

49 further group of sets having a different nucleotide in an additional common position, the nucleotides in the position of the oligonucleotide which are not in a common position being randomized;

(j) modifying the transcription factor with a linker moiety for attaching the transcription factor to a solid support;

(k) incubating each of said sets of oligonucleotides with the transcription factor under binding conditions to form oligonucleotide-transcription factor complexes;

(l) adding the competitor under binding conditions to form transcription factor-competitor complexes;

(m) attaching the transcription factor to a solid support via the linker moiety;

(n) separating bound from unbound competitor;

(o) detecting the binding of the competitor to the transcription factor attached to solid support where lowest binding is indicative of highest oligonucleotide specific binding activity;

(p) selecting the set having the highest activity; and (q) performing steps (i) through (p) iteratively until the sequence of at least one oligonucleotide having specific binding activity for the transcription factor has been determined.

18. The method of claim 17 wherein the step of attaching to the solid support comprises contacting transcription factor to a streptavidin-coated solid support, the linker moiety being biotin.

19. The method of claim 17 wherein the step of detecting the binding of the competitor comprises contacting each set of oligonucleotides with an antibody specific for the competitor.

20. The method of claim 17 wherein the transcription factor is c-myc and the competitor is a double stranded c-myc binding site wherein the first strand of the double stranded binding site is comprised of an oligonucleotide having the sequence (SEQ ID NO:28) and the second strand of the double stranded binding site is comprised of an oligonucleotide having the sequence (SEQ ID NO:29).

21. The method of claim 17 wherein the transcription factor is HIV-tat protein and the competitor is at least a portion of TAR.

22. The method of claim 17 wherein the transcription factor is c-rel and the competitor is the NF-kB binding site.

23. The method of claim 17 wherein the attaching step follows the incubation step.

24. A method for determining the sequence of an oligonucleotide having specific activity for a transcription factor comprising the steps of:

(a) preparing a group comprising a plurality of sets of oligonucleotides, each oligonucleotide comprising at least four nucleotides, by:
  i. defining a common position in the oligonucleotides of the sets, and
  ii. synthesizing said sets of oligonucleotides such that each set has a different nucleotide in said common position, the nucleotides which are not in said common position being randomized;

(b) preparing a competitor modified with a linker moiety for attaching the competitor to a solid support;

(c) incubating each of said sets of oligonucleotides with the transcription factor under binding conditions to form oligonucleotide-transcription factor complexes;

(d) adding a competitor under binding conditions to form transcription factor-competitor complexes;

(e) attaching the competitor to a solid support via the linker moiety;

50

(f) separating bound from unbound transcription factor;

(g) detecting binding of the transcription factor bound to the competitor where lowest binding is indicative of highest oligonucleotide specific binding activity;

(h) selecting the set having the highest activity;

(i) preparing a further group comprising a plurality of sets of oligonucleotides, each of the sets having in the previous common position the nucleotide appearing in the previously defined common position in the selected one of the previous group of sets; each set of said further group of sets having a different nucleotide in an additional common position, the nucleotides in the position of the oligonucleotide which are not in a common position being randomized;

(j) preparing the competitor modified with a linker moiety for attaching the competitor to a solid support;

(k) incubating each of said sets of oligonucleotides with the transcription factor under binding conditions to form oligonucleotide-transcription factor complexes;

(l) adding the competitor under binding conditions to form transcription factor-competitor complexes;

(m) attaching the competitor to a solid support via the linker moiety;

(n) separating bound from unbound transcription factor;

(o) detecting binding of the transcription factor to the competitor where lowest binding is indicative of highest oligonucleotide specific binding activity;

(p) selecting the set having the highest activity; and (q) performing steps (i) through (p) iteratively until the sequence of at least one oligonucleotide having specific binding activity for the transcription factor has been determined.

25. The method of claim 24 wherein the step of attaching to the solid support comprises contacting competitor to a streptavidin-coated solid support, the linker moiety being biotin.

26. The method of claim 24 wherein the step of detecting binding of the transcription factor comprises contacting each set of oligonucleotides with an antibody specific for the transcription factor.

27. The method of claim 24 wherein the transcription factor is c-myc and the competitor is a double stranded c-myc binding site wherein the first strand of the double stranded binding site is comprised of an oligonucleotide having the sequence (SEQ ID NO:28) and the second strand of the double stranded binding site is comprised of an oligonucleotide having the sequence (SEQ ID NO:29).

28. The method of claim 24 wherein the transcription factor is HIV-tat protein and the competitor is at least a portion of TAR.

29. The method of claim 24 wherein the transcription factor is c-rel and the competitor is the NF-kB binding site.

30. The method of claim 24 wherein the attachment step follows the incubation step.

31. A method for determining the sequence of an oligonucleotide having specific activity for a transcription factor comprising the steps of:

(a) preparing a group comprising a plurality of sets of oligonucleotides, each oligonucleotide comprising at least four nucleotides, by:
  i. defining a common position in the oligonucleotides of the sets, and
  ii. synthesizing said sets of oligonucleotides such that each set has a different nucleotide in said common position, the nucleotides which are not in said common position being randomized;

(b) modifying a first competitor with a linker moiety for attaching the first competitor to a solid support;

(c) incubating the transcription factor and the first competitor under binding conditions to form transcription factor-competitor complexes;

(d) incubating each of the sets of oligonucleotides with the transcription factor-competitor complex under binding conditions to form oligonucleotide-transcription factor-competitor complexes;

(e) adding a second competitor under binding conditions to form further complexes;

(f) attaching the first competitor to a solid support via the linker moiety;

(g) separating bound from unbound second competitor;

(h) detecting binding of the second competitor to the transcription factor where lowest binding is indicative of highest oligonucleotide specific binding activity;

(i) selecting the set having the highest activity;

(j) preparing a further group comprising a plurality of sets of oligonucleotides, each of the sets having in the previous common position the nucleotide appearing in the previously defined common position in the selected one of the previous group of sets; each set of said further group of sets having a different nucleotide in an additional common position, the nucleotides in the position of the oligonucleotide which are not in a common position being randomized;

(k) modifying the first competitor with a linker moiety for attaching the first competitor to a solid support;

(l) incubating the transcription factor and the first competitor under binding conditions to form transcription factor-competitor complexes;

(m) incubating each of the sets of oligonucleotides with the transcription factor-competitor complexes under binding conditions to form oligonucleotide-transcription factor-competitor complexes;

(n) adding the second competitor under binding conditions to form further complexes;

(o) attaching the first competitor to a solid support via the linker moiety;

(p) separating bound from unbound second competitor;

(q) detecting binding of the second competitor to the transcription factor where lowest binding is indicative of highest oligonucleotide specific binding activity;

(r) selecting the set having the highest activity; and (s) performing steps (j) through (r) iteratively until the sequence of at least one oligonucleotide having specific binding activity for the transcription factor has been determined.

32. The method of claim 31 wherein the step of attaching to the solid support comprises contacting the first competitor to a streptavidin-coated solid support, the linker moiety being biotin.

33. The method of claim 31 wherein the step of detecting binding of the second competitor comprises contacting each set of oligonucleotides with an antibody specific for the second competitor.

34. The method of claim 31 wherein the first competitor is an AP-1 binding site, the second competitor is fos nuclear protein and the transcription factor is jun nuclear protein.

35. The method of claim 31 wherein the attachment step follows the incubation step.

36. A method for determining the sequence of an oligonucleotide having specific activity for a transcription factor comprising the steps of:

(a) preparing a group comprising a plurality of sets of oligonucleotides, each oligonucleotide comprising at least four nucleotides, by:
  i. defining a common position in the oligonucleotides of the sets,
  ii. synthesizing said sets of oligonucleotides such that each set has a different nucleotide in said common position, the nucleotides which are not in said common position being randomized, and
  iii. detectably labeling oligonucleotides of each set of oligonucleotides;

(b) modifying a first competitor with a linker moiety for attaching the first competitor to a solid support;

(c) incubating the transcription factor and the first competitor under binding conditions to form transcription factor-competitor complexes;

(d) incubating each of the sets of oligonucleotides with the transcription factor-competitor complex under binding conditions to form oligonucleotide-transcription factor-competitor complexes;

(e) adding a second competitor under binding conditions to form further complexes;

(f) attaching the first competitor to a solid support via the linker moiety;

(g) separating bound from unbound second competitor;

(h) detecting binding of the oligonucleotide to the transcription factor where highest binding is indicative of highest oligonucleotide specific binding activity;

(i) selecting the set having the highest activity;

(j) preparing a further group comprising a plurality of sets of oligonucleotides, each of the sets having in the previous common position the nucleotide appearing in the previously defined common position in the selected one of the previous group of sets; each set of said further group of sets having a different nucleotide in an additional common position, the nucleotides in the position of the oligonucleotide which are not in a common position being randomized;

(k) detectably labeling oligonucleotides of each set of oligonucleotides;

(l) modifying the first competitor with a linker moiety for attaching the first competitor to a solid support;

(m) incubating the transcription factor and the first competitor under binding conditions to form transcription factor-competitor complexes;

(n) incubating each of the sets of oligonucleotides with the transcription factor-competitor complexes under binding conditions to form oligonucleotide-transcription factor-competitor complexes;

(o) adding the second competitor under binding conditions to form further complexes;

(p) attaching the first competitor to a solid support via the linker moiety;

(q) separating bound from unbound second competitor;

(r) detecting binding of the oligonucleotide to the transcription factor where highest binding is indicative of highest oligonucleotide specific binding activity;

(s) selecting the set having the highest activity; and (t) performing steps (j) through (s) iteratively until the sequence of at least one oligonucleotide having specific binding activity for the transcription factor has been determined.

37. The method of claim 36 wherein the step of attaching to the solid support comprises contacting the first competitor to a streptavidin-coated solid support, the linker moiety being biotin.

38. The method of claim 36 wherein the step of preparing a group comprising a plurality of sets of oligonucleotides comprises radiolabeling each set of oligonucleotides.

39. The method of claim 36 wherein the first competitor is an AP-1 binding site, the second competitor is fos nuclear protein and the transcription factor is jun nuclear protein.

40. The method of claim 36 wherein the attachment step follows the incubation step.

41. A method for determining the sequence of an oligonucleotide having specific activity for a target molecule comprising the steps of:
   (a) preparing a group comprising a plurality of sets of oligonucleotides, each oligonucleotide comprising at least four nucleotides, by:
      i. defining a common position in the oligonucleotides of the sets,
      ii. synthesizing said sets of oligonucleotides such that each set has a different nucleotide in said common position, the nucleotides which are not in said common position being randomized, and
      iii. modifying the oligonucleotides of the sets of oligonucleotides with linker moieties for attaching the oligonucleotides to a solid support;
   (b) incubating each of said sets of oligonucleotides with the target molecule under binding conditions to form oligonucleotide-target complexes;
   (c) attaching the sets of oligonucleotides to a solid support via the linker moiety;
   (d) separating bound from unbound target molecule;
   (e) detecting the binding of target molecule to each set of oligonucleotides attached to solid support where greatest binding is indicative of highest specific binding activity;
   (f) selecting the set having the highest activity;
   (g) preparing a further group comprising a plurality of sets of oligonucleotides, each of the sets having in the previous common position the nucleotide appearing in the previously defined common position in the selected one of the previous group of sets; each set of said further group of sets having a different nucleotide in an additional common position, the nucleotides in the position of the oligonucleotide which are not in a common position being randomized;
   (h) modifying the oligonucleotides of the sets of oligonucleotides with linker moieties for attaching the oligonucleotides to a solid support;
   (i) incubating each of said sets of oligonucleotides with the target molecule under binding conditions to form oligonucleotide-target complexes;
   (j) attaching the sets of oligonucleotides to a solid support via the linker moiety;
   (k) separating bound from unbound target molecule;
   (l) detecting the binding of target molecule to each set of oligonucleotides attached to solid support where greatest binding is indicative of highest specific binding activity;
   (m) selecting the set having the highest activity; and
   (n) performing steps (g) through (m) iteratively until the sequence of at least one oligonucleotide having specific binding activity for the target molecule has been determined.

42. The method of claim 41 wherein the step of attaching to the solid support comprises contacting sets of oligonucleotides to a streptavidin-coated solid support, the linker moiety being biotin.

43. The method of claim 41 wherein the step of detecting the binding of target molecule comprises contacting each set of oligonucleotides with an antibody specific for the target molecule.

44. The method of claim 41 further comprising a coincubating the sets of oligonucleotides with a competitor under binding conditions.

45. The method of claim 41 wherein the attaching step follows the incubation step.

46. A method for determining the sequence of an oligonucleotide having specific activity for a target molecule comprising the steps of:
   (a) preparing a group comprising a plurality of sets of oligonucleotides, each oligonucleotide comprising at least four nucleotides, by:
      i. defining a common position in the oligonucleotides of the sets,
      ii. synthesizing said sets of oligonucleotides such that each set has a different nucleotide in said common position, the nucleotides which are not in said common position being randomized, and
      iii. detectably labeling oligonucleotides of each set of oligonucleotides;
   (b) modifying the target molecule with a linker moiety for attaching the target molecule to a solid support;
   (c) incubating each of said sets of oligonucleotides with the target molecule under binding conditions to form oligonucleotide-target complexes;
   (d) attaching the target molecule to a solid support via the linker moiety;
   (e) separating bound from unbound oligonucleotide;
   (f) detecting the binding of each oligonucleotide set to the target molecule attached to solid support where greatest binding is indicative of highest specific binding activity;
   (g) selecting the set having the highest activity
   (h) preparing a further group comprising a plurality of sets of oligonucleotides, each of the sets having in the previous common position the nucleotide appearing in the previously defined common position in the selected one of the previous group of sets; each set of said further group of sets having a different nucleotide in an additional common position, the nucleotides in the position of the oligonucleotide which are not in a common position being randomized;
   (i) detectably labeling oligonucleotides of each set of oligonucleotides;
   (j) modifying the target molecule with a linker moiety for attaching the target molecule to a solid support;
   (k) incubating each of said sets of oligonucleotides with the target molecule under binding conditions to form oligonucleotide-target complexes;
   (l) attaching the target molecule to a solid support via the linker moiety;
   (m) separating bound from unbound oligonucleotide;
   (n) detecting the binding of each oligonucleotide set to target molecule attached to solid support where greatest binding is indicative of highest specific binding activity;
   (o) selecting the set having the highest activity; and
   (p) performing steps (h) through (o) iteratively until the sequence of at least one oligonucleotide having specific binding activity for the target molecule has been determined.

47. The method of claim 45 wherein the step of attaching to the solid support comprises contacting the target molecule to a streptavidin-coated solid support, the linker moiety being biotin.

48. The method of claim 45 wherein the step of preparing a group comprising a plurality of sets of oligonucleotides comprises radiolabeling each set of oligonucleotides.

49. The method of claim 45 further comprising coincubating the sets of oligonucleotides with a competitor under binding conditions.

50. The method of claim 45 wherein the attaching step follows the incubation step.

51. A method for determining the sequence of an oligonucleotide having specific activity for a target molecule comprising the steps of:
    (a) preparing a group comprising a plurality of sets of oligonucleotides, each oligonucleotide comprising at least four nucleotides, by:
        i. defining a common position in the oligonucleotides of the sets, and
        ii. synthesizing said sets of oligonucleotides such that each set has a different nucleotide in said common position, the nucleotides which are not in said common position being randomized;
    (b) modifying the target molecule with a linker moiety for attaching the target molecule to a solid support;
    (c) incubating each of said sets of oligonucleotides with the target molecule under binding conditions to form oligonucleotide-target complexes;
    (d) adding a competitor under binding conditions to form target-competitor complexes;
    (e) attaching the target molecule to a solid support via the linker moiety;
    (f) separating bound from unbound competitor;
    (g) detecting the binding of the competitor to the target molecule attached to solid support where lowest binding is indicative of highest oligonucleotide specific binding activity;
    (h) selecting the set having the highest activity;
    (i) preparing a further group comprising a plurality of sets of oligonucleotides, each of the sets having in the previous common position the nucleotide appearing in the previously defined common position in the selected one of the previous group of sets; each set of said further group of sets having a different nucleotide in an additional common position, the nucleotides in the position of the oligonucleotide which are not in a common position being randomized;
    (j) modifying the target molecule with a linker moiety for attaching the target molecule to a solid support;
    (k) incubating each of said sets of oligonucleotides with the target molecule under binding conditions to form oligonucleotide-target complexes;
    (l) adding the competitor under binding conditions to form target-competitor complexes;
    (m) attaching the target molecule to a solid support via the linker moiety;
    (n) separating bound from unbound competitor;
    (o) detecting the binding of the competitor to the target molecule attached to solid support where lowest binding is indicative of highest oligonucleotide specific binding activity;
    (p) selecting the set having the highest activity; and
    (q) performing steps (i) through (p) iteratively until the sequence of at least one oligonucleotide having specific binding activity for the target molecule has been determined.

52. The method of claim 51 wherein the step of attaching to the solid support comprises contacting target molecule to a streptavidin-coated solid support, the linker moiety being biotin.

53. The method of claim 51 wherein the step of detecting the binding of the competitor comprises contacting each set of oligonucleotides with an antibody specific for the competitor.

54. The method of claim 50 wherein the attaching step follows the incubation step.

55. A method for determining the sequence of an oligonucleotide having specific activity for a target molecule comprising the steps of:
    (a) preparing a group comprising a plurality of sets of oligonucleotides, each oligonucleotide comprising at least four nucleotides, by:
        i. defining a common position in the oligonucleotides of the sets, and
        ii. synthesizing said sets of oligonucleotides such that each set has a different nucleotide in said common position, the nucleotides which are not in said common position being randomized;
    (b) preparing a competitor modified with a linker moiety for attaching the competitor to a solid support;
    (c) incubating each of said sets of oligonucleotides with the target molecule under binding conditions to form oligonucleotide-target complexes,
    (d) adding a competitor under binding conditions to form target-competitor complexes;
    (e) attaching the competitor to a solid support via the linker moiety;
    (f) separating bound from unbound target molecule;
    (g) detecting binding of the target molecule bound to the competitor where lowest binding is indicative of highest oligonucleotide specific binding activity;
    (h) selecting the set having the highest activity;
    (i) preparing a further group comprising a plurality of sets of oligonucleotides, each of the sets having in the previous common position the nucleotide appearing in the previously defined common position in the selected one of the previous group of sets; each set of said further group of sets having a different nucleotide in an additional common position, the nucleotides in the position of the oligonucleotide which are not in a common position being randomized;
    (j) preparing the competitor modified with a linker moiety for attaching the competitor to a solid support;
    (k) incubating each of said sets of oligonucleotides with the target molecule under binding conditions to form oligonucleotide-target complexes;
    (l) adding the competitor under binding conditions to form target-competitor complexes;
    (m) attaching the competitor to a solid support via the linker moiety;
    (n) separating bound from unbound target molecule;
    (o) detecting binding of the target molecule to the competitor where lowest binding is indicative of highest oligonucleotide specific binding activity;
    (p) selecting the set having the highest activity; and
    (q) performing steps (i) through (p) iteratively until the sequence of at least one oligonucleotide having specific binding activity for the target molecule has been determined.

56. The method of claim 54 wherein the step of attaching to the solid support comprises contacting competitor to a streptavidin-coated solid support, the linker moiety being biotin.

57. The method of claim 54 wherein the step of detecting binding of the target molecule comprises contacting each set of oligonucleotides with an antibody specific for the target molecule.

58. The method of claim 54 wherein the attachment step follows the incubation step.

59. A method for determining the sequence of an oligonucleotide having specific activity for a target molecule comprising the steps of:

(a) preparing a group comprising a plurality of sets of oligonucleotides, each oligonucleotide comprising at least four nucleotides, by:
  i. defining a common position in the oligonucleotides of the sets, and
  ii. synthesizing said sets of oligonucleotides such that each set has a different nucleotide in said common position, the nucleotides which are not in said common position being randomized;

(b) modifying a first competitor with a linker moiety for attaching the first competitor to a solid support;

(c) incubating the target molecule and the first competitor under binding conditions to form target-competitor complexes;

(d) incubating each of the sets of oligonucleotides with the target-competitor complex under binding conditions to form oligonucleotide-target-competitor complexes;

(e) adding a second competitor under binding conditions to form further complexes;

(f) attaching the first competitor to a solid support via the linker moiety;

(g) separating bound from unbound second competitor;

(h) detecting binding of the second competitor to the target molecule where lowest binding is indicative of highest oligonucleotide specific binding activity;

(i) selecting the set having the highest activity;

(j) preparing a further group comprising a plurality of sets of oligonucleotides, each of the sets having in the previous common position the nucleotide appearing in the previously defined common position in the selected one of the previous group of sets; each set of said further group of sets having a different nucleotide in an additional common position, the nucleotides in the position of the oligonucleotide which are not in a common Position being randomized;

(k) modifying the first competitor with a linker moiety for attaching the first competitor to a solid support;

(l) incubating the target molecule and the first competitor under binding conditions to form target-competitor complexes;

(m) incubating each of the sets of oligonucleotides with the target-competitor complexes under binding conditions to form oligonucleotide-target-competitor complexes;

(n) adding the second competitor under binding conditions to form further complexes;

(o) attaching the first competitor to a solid support via the linker moiety;

(p) separating bound from unbound second competitor;

(q) detecting binding of the second competitor to the target molecule where lowest binding is indicative of highest oligonucleotide specific binding activity;

(r) selecting the set having the highest activity; and (s) performing steps (j) through (r) iteratively until the sequence of at least one oligonucleotide having specific binding activity for the target molecule has been determined.

60. The method of claim 58 wherein the step of attaching to the solid support comprises contacting the first competitor to a streptavidin-coated solid support, the linker moiety being biotin.

61. The method of claim 58 wherein the step of detecting binding of the second competitor comprises contacting each set of oligonucleotides with an antibody specific for the second competitor.

62. The method of claim 58 wherein the first competitor is an AP-1 binding site, the second competitor is fos nuclear protein and the target molecule is jun nuclear protein.

63. The method of claim 58 wherein the attachment step follows the incubation step.

64. A method for determining the sequence of an oligonucleotide having specific activity for a target molecule comprising the steps of:

(a) preparing a group comprising a plurality of sets of oligonucleotides, each oligonucleotide comprising at least four nucleotides, by:
  i. defining a common position in the oligonucleotides of the sets,
  ii. synthesizing said sets of oligonucleotides such that each set has a different nucleotide in said common position, the nucleotides which are not in said common position being randomized, and
  iii. detectably labeling oligonucleotides of each set of oligonucleotides;

(b) modifying a first competitor with a linker moiety for attaching the first competitor to a solid support;

(c) incubating the target molecule and the first competitor under binding conditions to form target-competitor complexes;

(d) incubating each of the sets of oligonucleotides with the target-competitor complex under binding conditions to form oligonucleotide-target-competitor complexes;

(e) adding a second competitor under binding conditions to form further complexes;

(f) attaching the first competitor to a solid support via the linker moiety;

(g) separating bound from unbound second competitor;

(h) detecting binding of the oligonucleotide to the target molecule where highest binding is indicative of highest oligonucleotide specific binding activity;

(i) selecting the set having the highest activity;

(j) preparing a further group comprising a plurality of sets of oligonucleotides, each of the sets having in the previous common position the nucleotide appearing in the previously defined common position in the selected one of the previous group of sets; each set of said further group of sets having a different nucleotide in an additional common position, the nucleotides in the position of the oligonucleotide which are not in a common position being randomized;

(k) detectably labeling oligonucleotides of each set of oligonucleotides;

(l) modifying the first competitor with a linker moiety for attaching the first competitor to a solid support;

(m) incubating the target molecule and the first competitor under binding conditions to form target-competitor complexes;

(n) incubating each of the sets of oligonucleotides with the target-competitor complex under binding conditions to form oligonucleotide-target-competitor complexes;

(o) adding the second competitor under binding conditions to form further complexes;

(p) attaching the first competitor to a solid support via the linker moiety;

(q) separating bound from unbound second competitor;

(r) detecting binding of the oligonucleotide to the target molecule where highest binding is indicative of highest oligonucleotide specific binding activity;

(s) selecting the set having the highest specific binding activity; and (t) performing steps (j) through (s) iteratively until the sequence of at least one oligonucleotide having specific binding activity for the target molecule has been determined.

65. The method of claim 63 wherein the step of attaching to the solid support comprises contacting the first competitor to a streptavidin-coated solid support, the linker moiety being biotin.

66. The method of claim 63 wherein the step of preparing a group comprising a plurality of sets of oligonucleotides comprises radiolabeling each set of oligonucleotides.

67. The method of claim 63 wherein the first competitor is an AP-1 binding site, the second competitor is fos nuclear protein and the target molecule is jun nuclear protein.

68. The method of claim 63 wherein the attachment step follows the incubation step.

* * * * *

UNITED STATES PATENT AND TRADEMARK OFFICE
CERTIFICATE OF CORRECTION

PATENT NO. : 5,747,253
DATED : May 5, 1998
INVENTOR(S) : Ecker et al.

It is certified that error appears in the above-indentified patent and that said Letters Patent is hereby corrected as shown below:

Col. 31, line 18, please delete "BiIm" and insert therefor --biIm--;
Col. 55, line 1, please delete "45" and insert therefor --46--;
Col. 55, line 5, please delete "45" and insert therefor --46--;
Col. 55, line 8, please delete "45" and insert therefor --46--;
Col. 55, line 11, please delete "45" and insert therefor --46--;
Col. 56, line 9, please delete "50" and insert therefor --51--;
Col. 56, line 64, please delete "54" and insert therefor --55--;
Col. 57, line 44, please delete "Position" and insert therefor --position--;
Col. 58, line 1, please delete "58" and insert therefor --59--;
Col. 58, line 5, please delete "58" and insert therefor --59--;
Col. 58, line 9, please delete "58" and insert therefor --59--;
Col. 58, line 12, please delete "58" and insert therefor --59--;
Col. 60, line 1, please delete "63" and insert therefor --64--;
Col. 60, line 5, please delete "63" and insert therefor --64--;
Col. 60, line 8, please delete "63" and insert therefor --64--;
Col. 60, line 11, please delete "63" and insert therefor --64--.

Signed and Sealed this

Twenty-eighth Day of December, 1999

Q. TODD DICKINSON

*Attest:*

*Attesting Officer*  *Acting Commissioner of Patents and Trademarks*